United States Patent
Kley

(10) Patent No.: US 6,265,711 B1
(45) Date of Patent: *Jul. 24, 2001

(54) SCANNING PROBE MICROSCOPE ASSEMBLY AND METHOD FOR MAKING SPECTROPHOTOMETRIC NEAR-FIELD OPTICAL AND SCANNING MEASUREMENTS

(75) Inventor: Victor B. Kley, Berkeley, CA (US)

(73) Assignee: General Nanotechnology L.L.C., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/906,602

(22) Filed: Dec. 10, 1996

Related U.S. Application Data

(63) Continuation of application No. 08/281,883, filed on Jul. 28, 1994, now abandoned.

(51) Int. Cl.[7] .......................... H01J 37/00; G01N 29/122
(52) U.S. Cl. ........................ 250/234; 250/306; 250/307
(58) Field of Search .................... 250/234, 235, 250/216, 306, 307, 227.11, 236, 226, 310, 311; 356/373, 375, 376; 378/98.2, 98.5, 98.6; 359/368, 393, 525; 364/525; 382/128, 130, 131, 254; 348/29, 79; 395/961, 131, 129, 334; 345/150, 153, 145, 146, 133, 140

(56) References Cited

U.S. PATENT DOCUMENTS

| | | |
|---|---|---|
| Re. 32,457 | 7/1987 | Matey . |
| Re. 34,708 | 8/1994 | Hansma et al. . |
| 3,812,288 | 5/1974 | Walsh et al. . |
| 4,604,520 | 8/1986 | Pohl . |
| 4,672,559 | 6/1987 | Jansson et al. . |
| 4,673,477 | * 6/1987 | Ramalingan et al. .......... 204/192.38 |
| 4,681,451 | 7/1987 | Guerra et al. . |
| 4,697,594 | 10/1987 | Mayo, Jr. . |
| 4,866,986 | 9/1989 | Cichanski . |
| 4,924,091 | 5/1990 | Hansma et al. . |

(List continued on next page.)

OTHER PUBLICATIONS

E.I. Givargizov et al, "Growth of diamond particles on sharpened silicon tips," *Materials Letters*, vol. 18, No. 1,2, Nov. 1993.

R.B. Watson, et al, "The Radiation Patterns of Dielectric Rods—Experiment and Theory," *Journal of Applied Physics*, vol. 19, Jul., 1948.

Eric Betzig et al, "Near–Field Optics: Microscopy, Spectroscopy, and Surface Modification Beyond the Diffraction Limit," *Science* vol. 257, Jul. 10, 1992.

N.F. van Hulst et al, "Near–field optical microscope using a silicon–nitride probe," *Appl. Phys. Lett.* 62(5), Feb. 1, 1993.

R. Toledo–Crow et al, "Near–field differential scanning optical microscope with atomic force regulation," *Appl. Phys. Lett.* 60 (24), Jun. 15, 1992.

Watson, R.B., et al., "The Radiation Patterns of Dielectric Rods—Experiment and Theory", *Journal of Applied Physics*, 19:661–670 (1948).

Davis, Robert F., "Depostion, characterization, and device developement in diamond, silicon carbide, and gallium nitride thin films", *J. Vac. Sci. Technol.*, A11(4):829–837 (1993).

*Primary Examiner*—John R. Lee
(74) *Attorney, Agent, or Firm*—Townsend and Townsend and Crew LLP

(57) ABSTRACT

A scanning probe microscope assembly that has an atomic force measurement (AFM) mode, a scanning tunneling measurement (STM) mode, a near-field spectrophotometry mode, a near-field optical mode, and a hardness testing mode for examining an object.

61 Claims, 30 Drawing Sheets

U.S. PATENT DOCUMENTS

| | | | |
|---|---|---|---|
| 5,001,344 | * | 3/1991 | Kato et al. .............................. 250/307 |
| 5,018,865 | * | 5/1991 | Ferrell et al. ......................... 356/376 |
| 5,105,305 | | 4/1992 | Betzig et al. . |
| 5,155,589 | | 10/1992 | Gere . |
| 5,254,854 | | 10/1993 | Betzig . |
| 5,319,977 | | 6/1994 | Quate et al. . |
| 5,354,985 | * | 10/1994 | Quate .................................... 250/234 |
| 5,357,110 | | 10/1994 | Statham . |
| 5,362,963 | * | 11/1994 | Kopelman et al. ................... 250/307 |
| 5,393,647 | * | 2/1995 | Neukermans et al. ........... 250/307 X |
| 5,495,109 | * | 2/1996 | Lindsay et al. ...................... 250/306 |
| 5,502,306 | | 3/1996 | Meisburger et al. . |

\* cited by examiner

SCANNING PROBE MICROSCOPE ASSEMBLY AND METHOD FOR MAKING SPECTROPHOTOMETRIC NEAR-FIELD OPTICAL AND SCANNING MEASUREMENTS

This is a continuation, of application Ser. No. 08/281,883 filed Jul. 28, 1994, now abandoned.

The present invention relates generally to spectrophotometry, near-field microscopy, and scanning probe microscopy. Specifically, it relates to a scanning probe microscope assembly and corresponding method for making spectrophotometric and near-field measurements in addition to conventional scanning probe measurements.

BACKGROUND OF THE INVENTION

In the past, near-field optical microscopes, such as those described in U.S. Pat. No. 4,604,520, have incorporated spectrophotometer in order to obtain information about the composition of the specimen being examined. However, they are plagued by the extremely slow rate at which the specimen area can be scanned. This problem has severely limited the use of near-field optical microscopes and spectrophotometer for commercially important applications in the biological and industrial fields. In addition, near-field optical microscopes can not achieve the resolution of scanning probe microscopes.

On the other hand conventional scanning probe microscopes, such as scanning tunneling microscopes and atomic force microscopes, have been able to make only limited determinations of the constituents of an object under inspection. Moreover, these conventional scanning probe microscopes cannot define the structure of the object below its surface and cannot define with fine resolution pits, walls, projections, and other structures which prevent the end of the probe tip from coming close enough to the object in these areas for accurate inspection by conventional scanning probe microscopy.

U.S. Pat. No. 5,319,977 describes a scanning probe microscope that utilizes the probe tip to make acoustic microscopy measurements and either atomic force microscopy (AFM) measurements or scanning tunneling microscopy (STM) measurements during the same scanning sequence. The resolution of acoustic microscopy is however rather low in comparison to AFM, STM, or near-field optical microscopy. Moreover, as with conventional scanning probe microscopes, the scanning probe microscope described in U.S. Pat. No. 5,319,977 cannot define those types of structures which prevent the end of the probe tip from coming close enough to the object for accurate inspection.

Furthermore, many objects exhibit areas of varying composition and conductivity. For example, the surface of a semiconductor may change from being conductive to insulative as a function of position. However, no scanning probe microscopes currently exist which are capable of making STM, AFM, near-field optical microscopy, and spectrophotometric measurements during the same scanning sequence in order to properly image and identify such an object.

SUMMARY OF THE INVENTION

The foregoing problems are solved by a scanning probe microscope assembly that has an AFM mode, an STM mode, a near-field spectrophotometry mode, a near-field optical mode, and a hardness testing mode for examining an object.

The scanning probe microscope assembly includes a probe having a base. The probe also includes a cantilever connected to the base, a tip connected to the cantilever, and a clamp connected to the base.

The scanning probe microscope assembly is configured to induce atomic force interaction between the tip and the object and to detect deflection of the cantilever due to the atomic force interaction during the AFM.

The scanning probe microscope assembly is also configured to induce and detect a tunneling current between the tip and the object during the STM mode. During the STM mode, the cantilever is held rigid with respect to the base.

The scanning probe microscope assembly includes a spectrophotometer which has a light source optically coupled to the tip. The light source is controlled to provide light to the tip during the spectrophotometry mode. The tip is shaped so that it emits the provided light at the sharp end of the tip. The emitted light then optically interacts with the object. The spectrophotometer includes a photodetector for detecting light that results from the emitted light optically interacting with the object in order to make spectrophotometric measurements of the detected light.

The scanning probe microscope assembly is also configured to rotationally polarize the light provided by the light source of the spectrophotometer during the near-field mode. The scanning probe microscope assembly identifies deep surface features based on the light detected by the photodetector that results from the rotationally polarized light being emitted by the tip and optically interacting with the object.

The scanning probe microscope assembly is also configured to direct the tip to penetrate the object at a specific point with a predefined known force. The light source is controlled to provide light to the tip during the hardness testing mode before and while the tip penetrates the object. The photodetector detects the light that results from the emitted light optically interacting with the object before and while the tip penetrates the object. The scanning probe microscope assembly compares the resulting light detected before the tip penetrates the object with the resulting light detected while the tip penetrates the object to determine the hardness of the object.

BRIEF DESCRIPTION OF THE DRAWINGS

The invention will be more readily apparent from the following detailed description and appended claims when taken in conjunction with the drawings, in which:

FIG. 12b shows the operation of the mode shifter and lens of FIG. 12a;

DESCRIPTION OF THE FIRST EMBODIMENT

Figure 1:
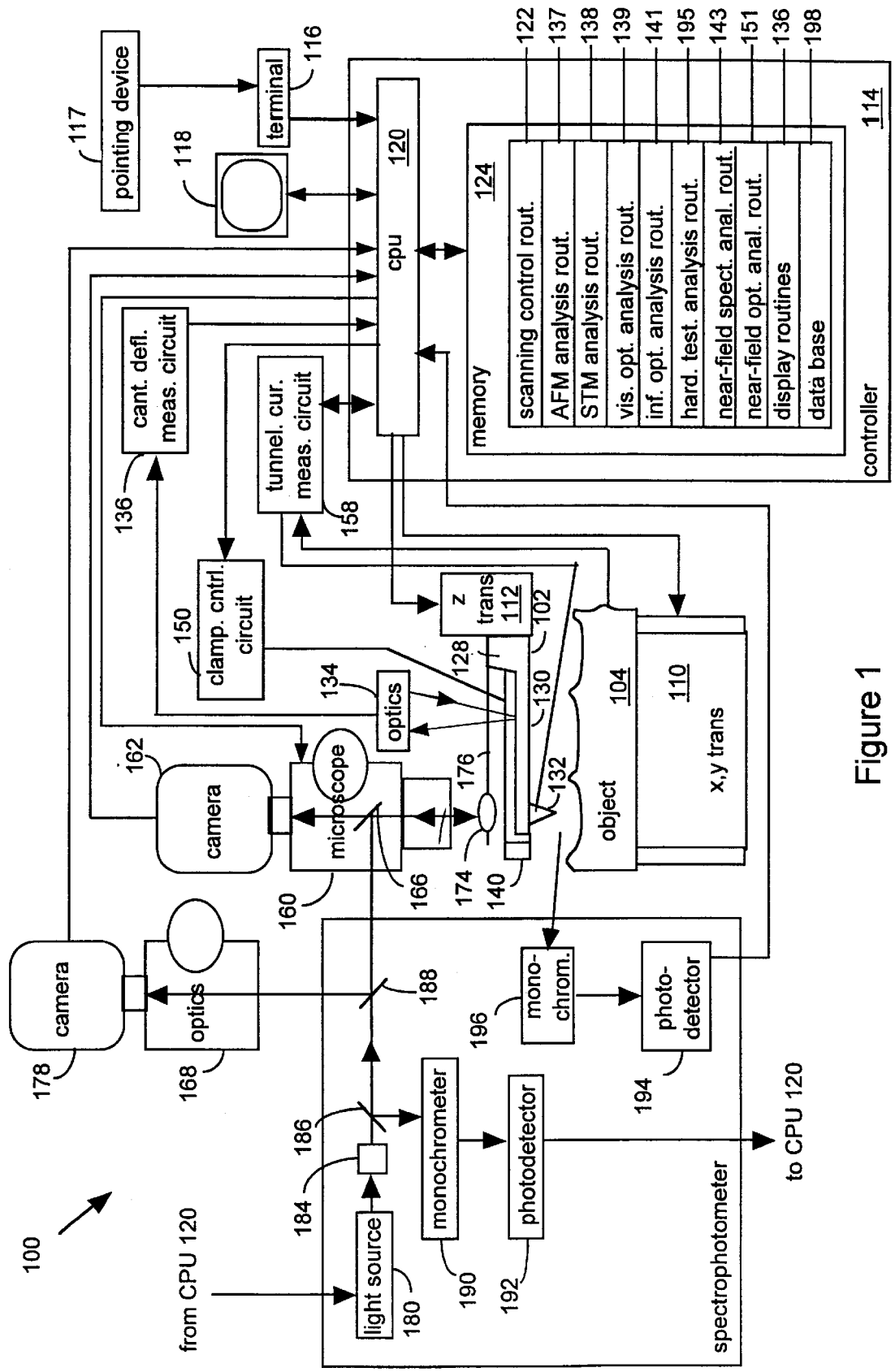
FIG. 1 shows a conceptual view of a scanning probe microscope assembly in accordance with the present invention.

Referring to FIG. 1, there is shown a conceptual diagram of one embodiment of a scanning probe microscope assembly 100 in accordance with the present invention.

A probe 102 is used to scan the surface of an object 104 in variety of measurement modes, as will be discussed shortly. In the preferred embodiment, the surface of the object 104 is scanned by probe 102 using a conventional piezoelectric XY translator 110 to move the object 104 along the X and Y axes and a conventional piezoelectric Z translator 112 to move the probe 102 along the Z axis. However, those skilled in the art will appreciate that a piezoelectric XYZ translator may be used instead to move the object 104 along the X, Y, and Z axes while the probe 102 remains stationary. Alternatively, a piezoelectric XYZ translator may be used to move the probe 102 along the X, Y, and Z axes while the object 104 remains stationary.

Scanning is controlled by controller or computer 114 based on inputs received from the control terminal 116. During scanning, controller 114 analyzes measurement data and displays measurement information on display monitor 118.

Atomic Force Microscopy Mode

Scanning probe microscope assembly 100 is configured to perform atomic force microscopy (AFM). As will be explained later, the AFM mode may occur when the user has selected the AFM mode with the control terminal 116 and also issues with the control terminal 116 a high magnification zoom control signal received by the CPU 120 for a high magnification scan of the object 104. The scanning control routine 122 stored in the memory 124 and run on the CPU 120 then generates scanning control signals outputted by the CPU 120 for controlling the XY and Z translators 110 and 112 to position probe 102 over the surface of the object 104 for AFM measurements.

Probe 102 includes a base 128 coupled to the Z translator 112, a cantilever 130 integrally connected to the base 128, and a sharp projecting tip 132 integrally connected to the cantilever 130. The scanning control signals generated by the scanning control routine 122 control the XY and Z translators 110 and 112 so that tip 132 is positioned in close proximity to or in contact with the object 104 depending on what type of force interaction between the tip 132 and the object 104 is desired. As a result, the cantilever 130 will be deflected due to a non-optical interaction in the form of a atomic force interaction between the tip 132 and the object 104. As those skilled in the art know, this atomic force interaction may be due to Van der Waals forces, magnetic forces, electrostatic forces, lateral forces, or other related forces.

The deflection of the cantilever 130 representing the atomic force interaction between the tip 132 and the object 104 is optically detected by conventional optics 134. The conventional deflection measurement circuit 136 is coupled to the optics 134. It measures the optically detected deflection and outputs a deflection measurement signal containing data representing the measured deflection. The measured deflection also corresponds to the topography of the object. Thus, the optics 134 and the deflection measurement circuit 135 serve as a cantilever deflection measurer. Those skilled in the art will appreciate that other types of systems may be used to measure deflection of the cantilever 130.

The deflection measurement signal is provided to the CPU 120. The data contained by the signal is analyzed and processed by the AFM analysis routine 137 to produce AFM image data representing a high magnification (or nanoview) image of the topography of the object 104. The display routine 136 then formats the AFM image data, in the way described later, and the CPU 120 provides it to the display monitor 118 for display. The routines 136 and 137 are both stored in the memory 124 and run on the CPU 120.

Scanning Tunneling Microscopy Mode

The scanning probe microscope assembly 100 of FIG. 1 is configured also to perform scanning tunneling microscopy (STM). Like the AFM mode, the STM mode may occur when the user selects with the control terminal 116 the STM mode and also issues with control terminal 116 a high magnification zoom control signal received by the CPU 120 for a high magnification scan of the object 104. During this scan, the scanning control routine 122 generates scanning control signals outputted by the CPU 120 for controlling the XY and Z translators 110 and 112 to position probe 102 over the surface of the object 104 for STM measurements.

Figure 2A:
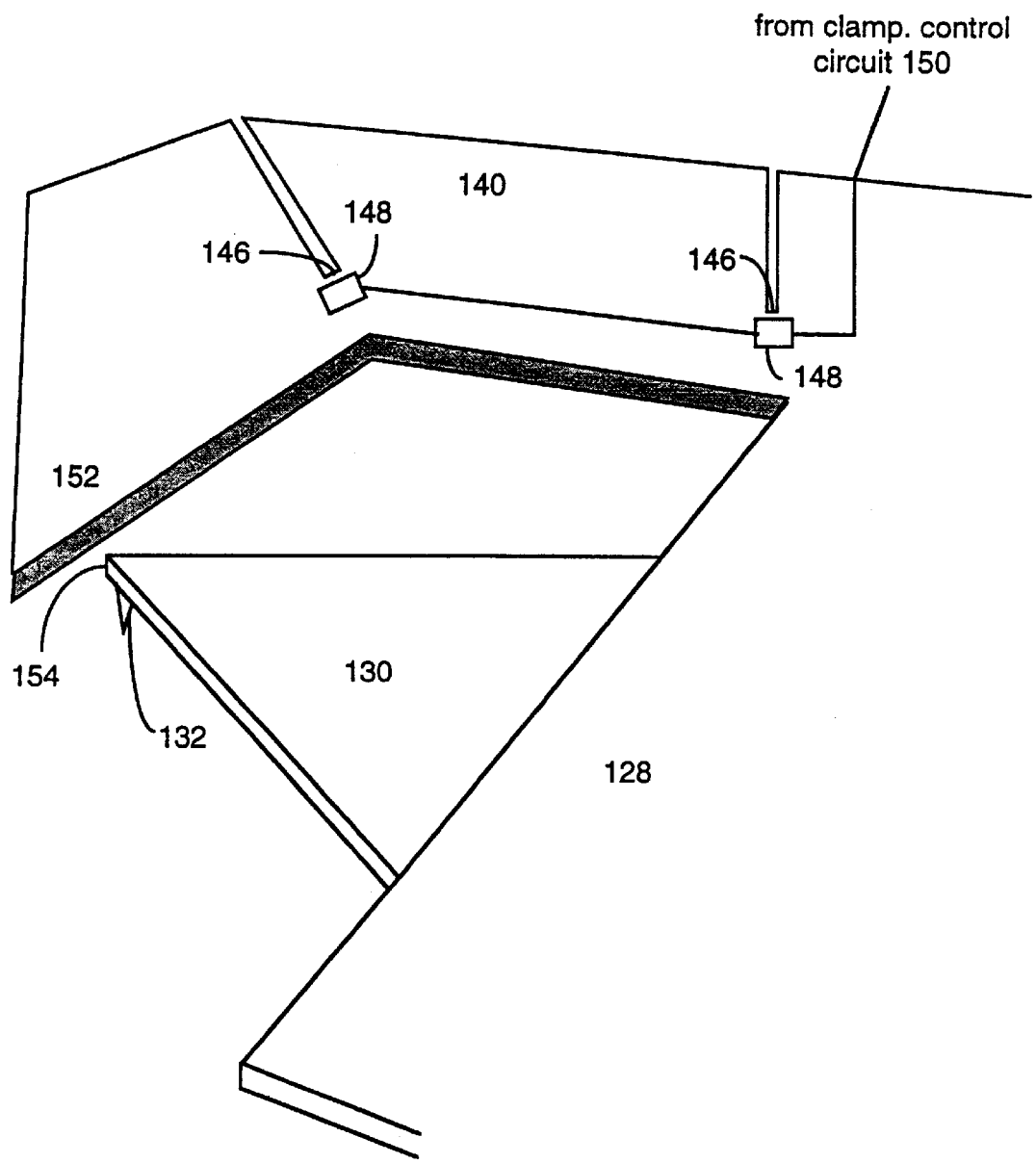
FIGS. 2a and 2b show embodiments of a clamping structure for holding rigid the cantilever of the probe of the scanning probe microscope assembly of FIG. 1 during a scanning tunneling measurement (STM) mode.

Referring to FIG. 2a, probe 102 includes, in addition to the base 128, the cantilever 130, and the tip 132, a clamp in the form of a clamping arm 140 integrally connected to the base 128. The lens system 174 and the lens system support 176 of the probe 102, which are shown in FIG. 2c and described later, are not shown in FIG. 2a for ease of illustration. The clamping arm 140 is L-shaped and extends out from the base 128 past and adjacent to the free end 142 of the cantilever 130. The clamping arm 140 has slots 144 which form action joints 146 at the closed ends of the slots 144.

In one embodiment, heating elements 148 are disposed on the clamping arm 140 at the action joints 146, as shown in FIG. 2a. Referring to FIG. 1, when the user selects the STM mode with the control terminal 116, the scanning control routine 122 generates a clamping control signal received by the clamping control circuit 150. In response, the clamping control circuit 150 generates clamping arm movement signal provided to the heating elements 148 shown in FIG. 2a. The heating elements 148 are responsive to the clamping arm movement signal and heat the action joints 146 so that the clamping arm 140 thermally expands at the action joints 146 and the free end 152 of the clamping arm 140 moves in and presses firmly against the free end 154 of the cantilever 130. As a result, the cantilever 130 in the STM mode is immobilized and held rigidly against the clamping arm 140 so that STM can be performed with tip 132, as will be described shortly.

Figure 2B:
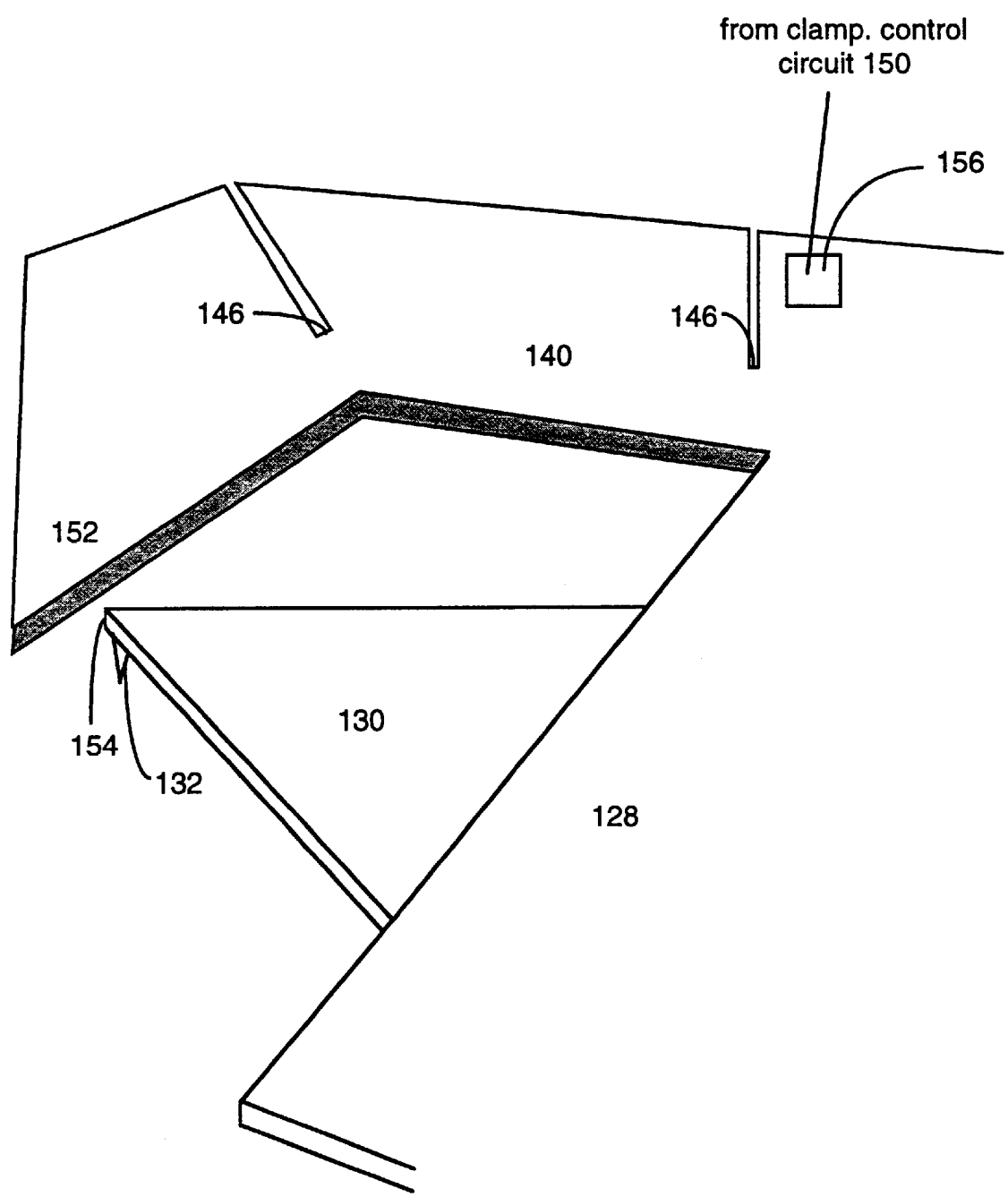
Figure 2C:
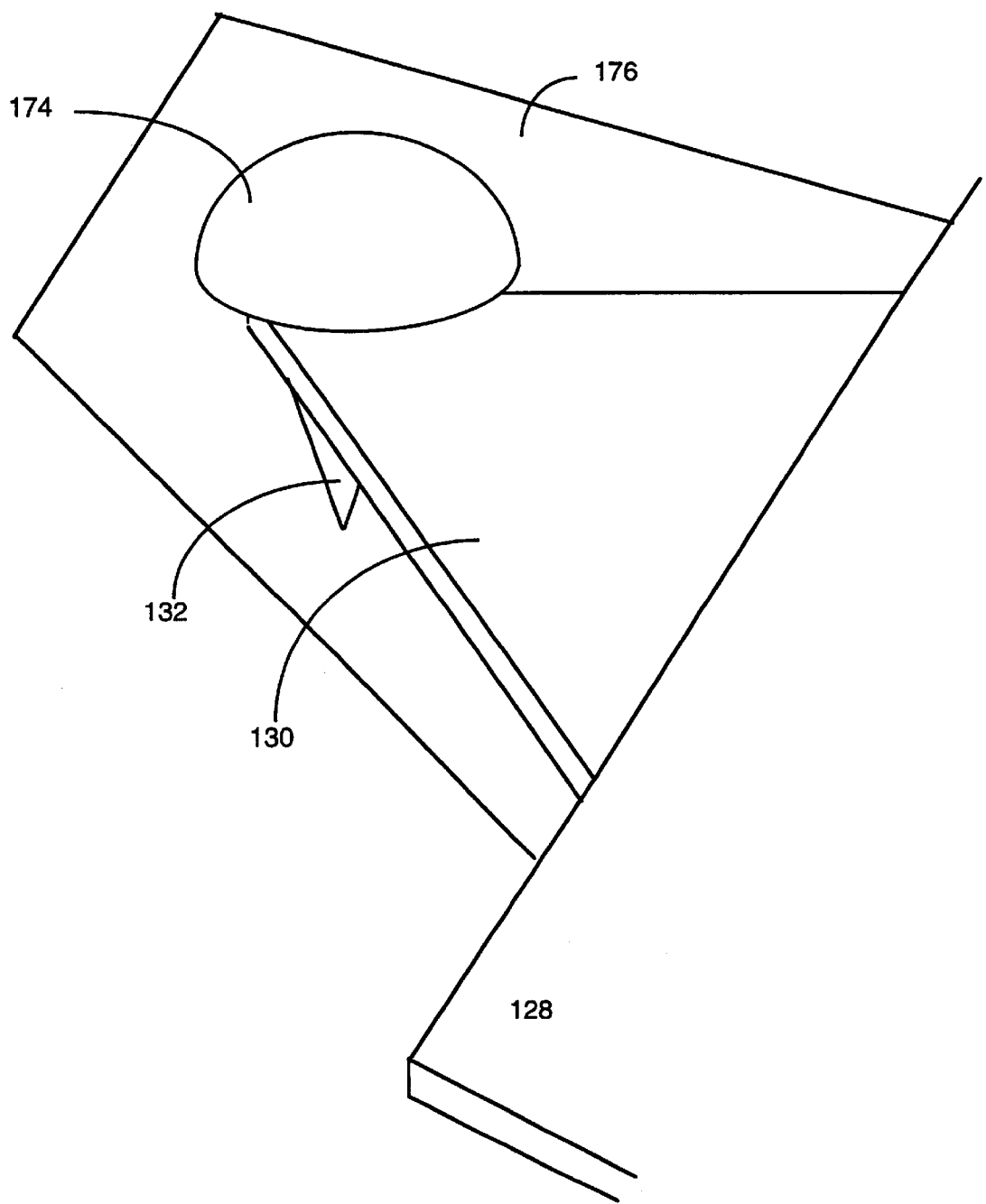
FIG. 2c shows the probe of the scanning probe microscope assembly of FIG. 2a or 2b with an attached refractive lens over the tip of the probe.

Alternatively, an electrode 156 may be fixed to the clamping arm 140, as shown in FIG. 2b. In response to the clamping arm movement signal provided by the clamping control circuit 150 of FIG. 1, the electrode 156 applies an electrostatic charge to the clamping arm 140. As in the embodiment of FIG. 2a, the clamping arm 140 expands at the action joints 146 so that the free end 152 of the clamping arm 140 moves in and presses against the free end 154 of the cantilever 132.

Figure 3A:
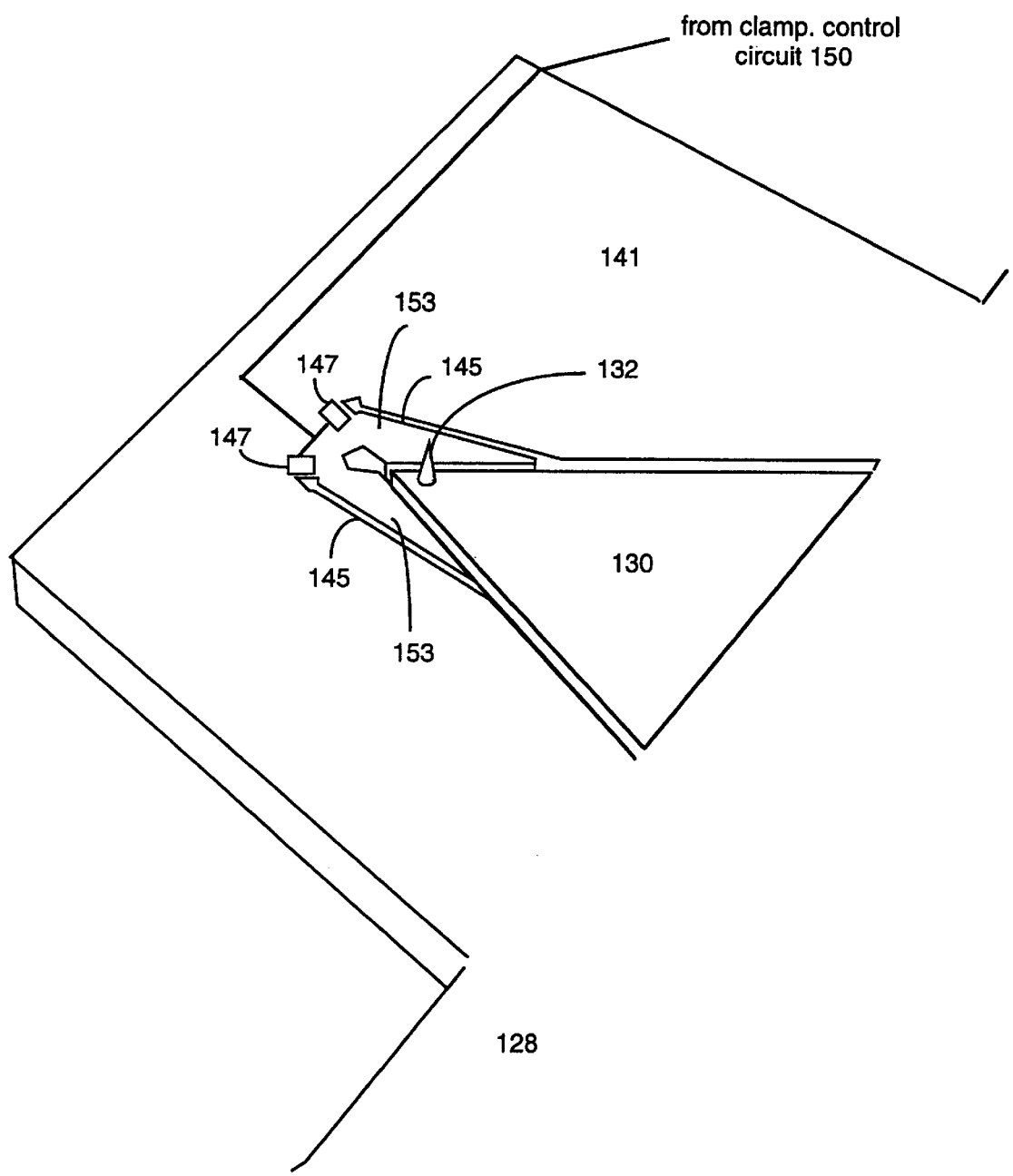
FIGS. 3a and 3b show still other embodiments of a clamping structure for holding rigid the cantilever of the scanning probe, microscope assembly of FIG. 1 during the STM mode.

FIG. 3a shows an alternative clamp in the form of a clamping structure 141 that is integrally formed with the base 128 and surrounds the cantilever 130. The clamping structure 141 has slots 145 which form action joints 147 at the closed ends of the slots 145.

Similar to the embodiment of FIG. 2a, heating elements 149 are disposed on the clamping structure 141 at the action joints 147. When the user has selected the STM mode, the clamping control circuit 150 provides a clamping structure movement signal to the heating elements 149. The heating elements 149 heat the action joints 147 so that the clamping structure 141 expands at the action joints 147 and the clamping arms 153 of the clamping structure 141 move in and press firmly against the sides of the cantilever 130.

Figure 3B:
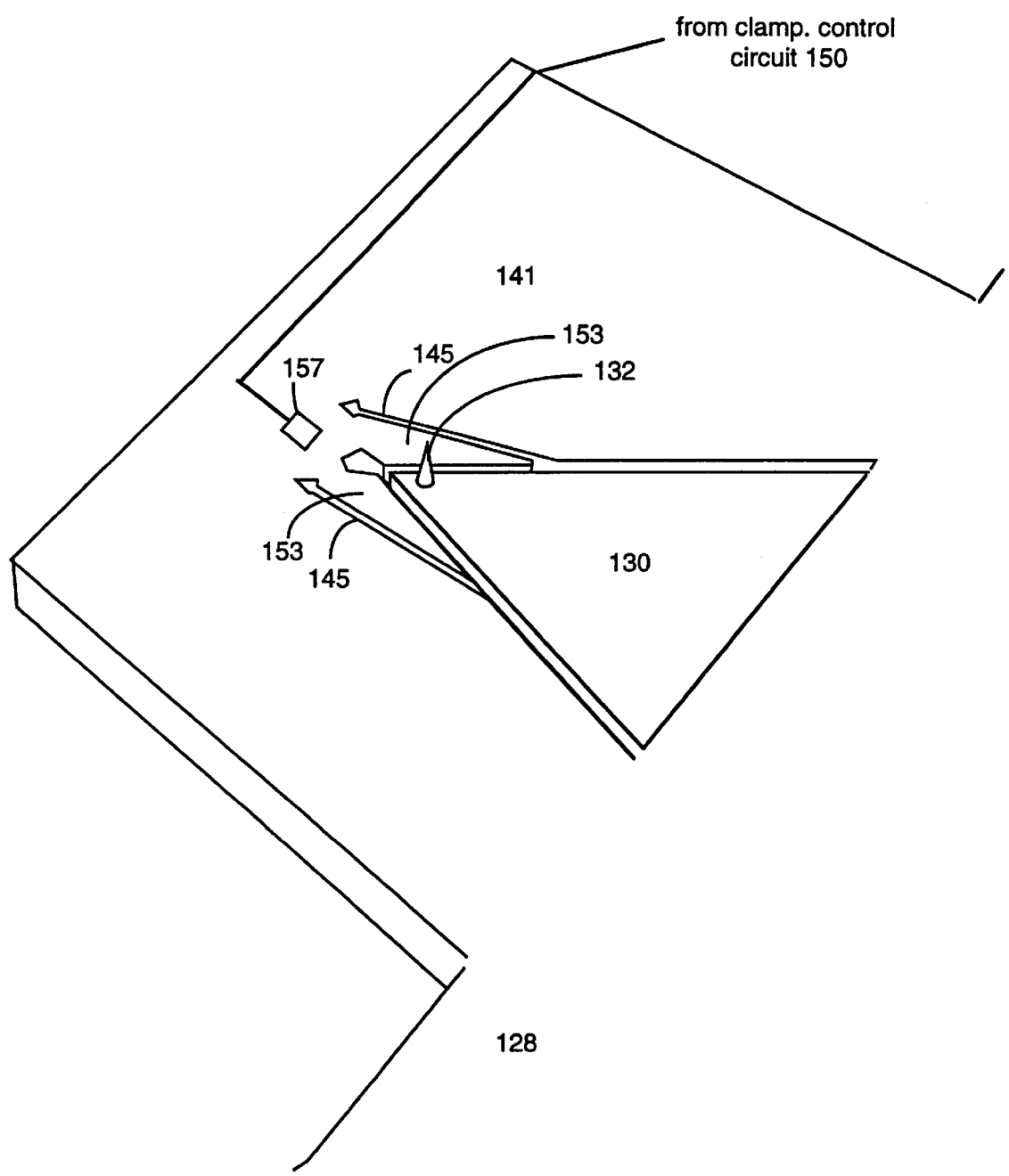

Alternatively, an electrode 157 may be fixed to the clamping structure 141, as shown in FIG. 3b. Similar to the embodiment of FIG. 2b, the electrode 157 applies an electrostatic charge to the clamping structure 141 in response to the clamping structure movement signal provided by the clamping control circuit 150. Like in the embodiment of FIG. 4, the clamping structure 141 expands at the action joints 147 and the clamping arms 153 move in and press against the sides of the cantilever 130.

Figure 3C:
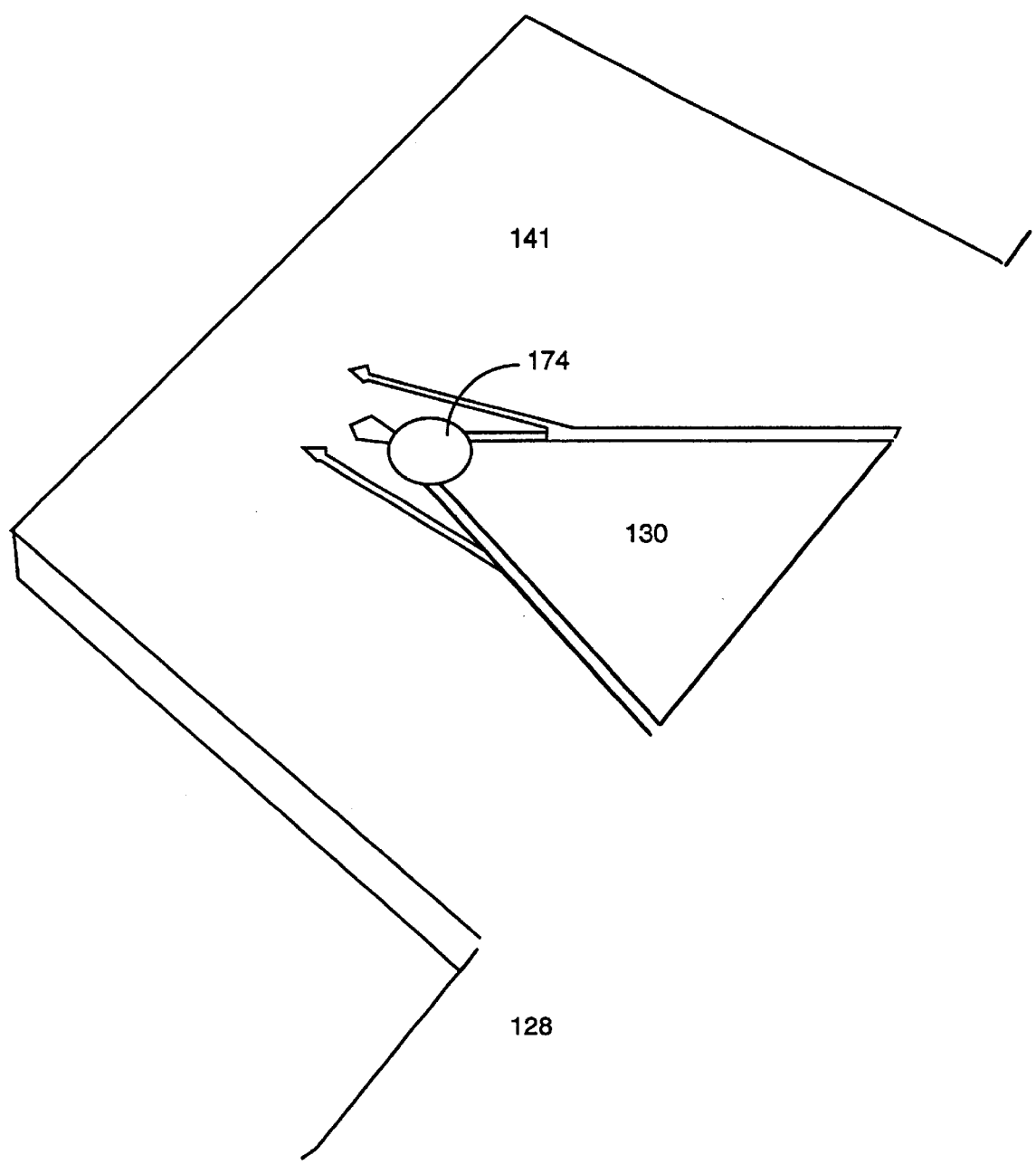
FIG. 3c shows the probe of the scanning probe microscope assembly of FIGS. 3a or 3b with an attached refractive lens over the tip of the probe.

As shown in FIG. 3c, the clamping structure 141 of FIGS. 3a and 3b serves as a shelf and support for the lens 174 which may be independent from or integrally formed with the clamping structure 141. The optical operation of the lens 174 will be described later.

Figure 4A:
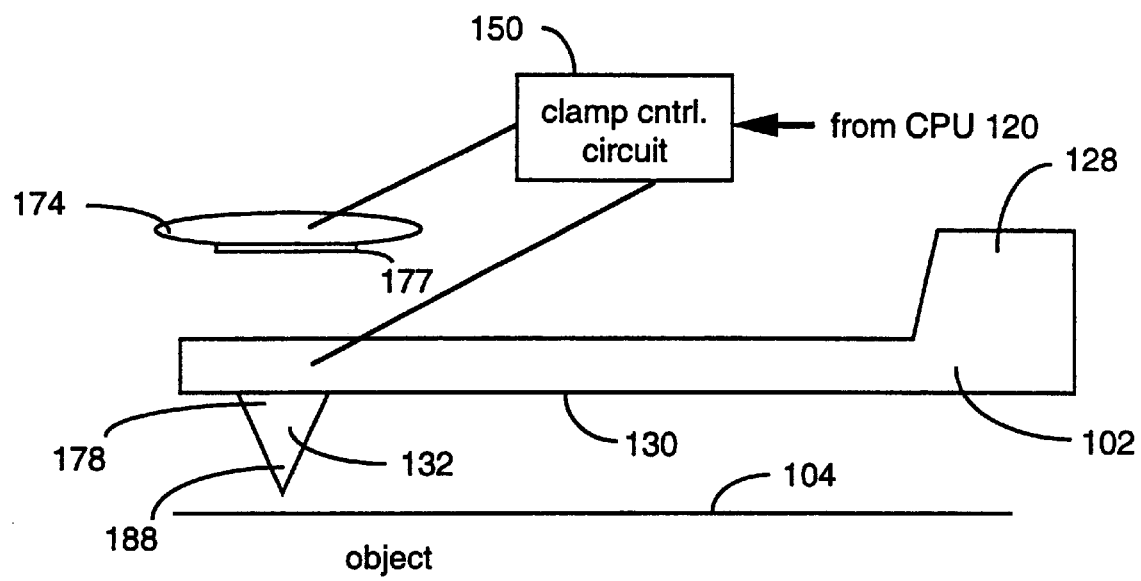
FIGS. 4a and 4b show further embodiments of a clamping device for holding rigid the cantilever of the scanning probe microscope assembly of FIG. 1 during the STM mode.
Figure 4B:
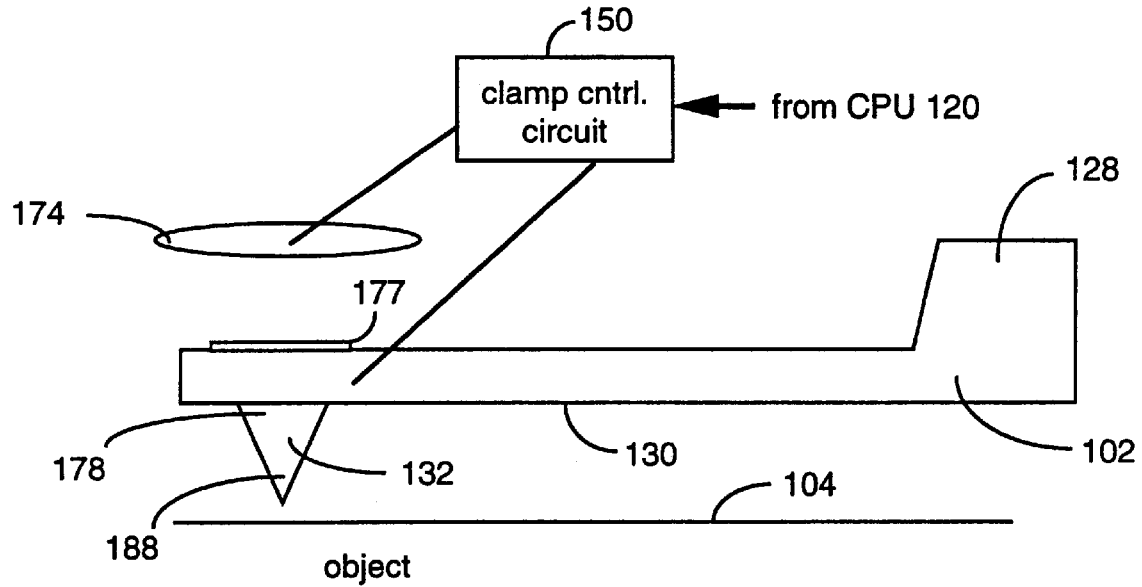

Referring to FIGS. 4a and 4b, the lens 174 can be used to provide clamping of the cantilever 130 alone or in conjunction with the embodiments of FIGS. 3a and 3b. As shown in FIGS. 4a and 4b, an optically transparent insulating layer 177, such as silicon dioxide, is formed on the lower surface of the lens 174 (or similar support member) or the upper surface of the cantilever 130. In the STM mode, the clamping control circuit 150 applies an appropriate voltage between the lens 174 and the cantilever 130 so as to form a capacitive structure which electrostatically clamps the motion of the cantilever 130. Those skilled in the art will appreciate that this configuration can additionally be used to damp, drive, or detect the motion of the cantilever 130 depending on which of the modes of operation described herein is being employed by scanning probe microscope 100.

Figure 5:
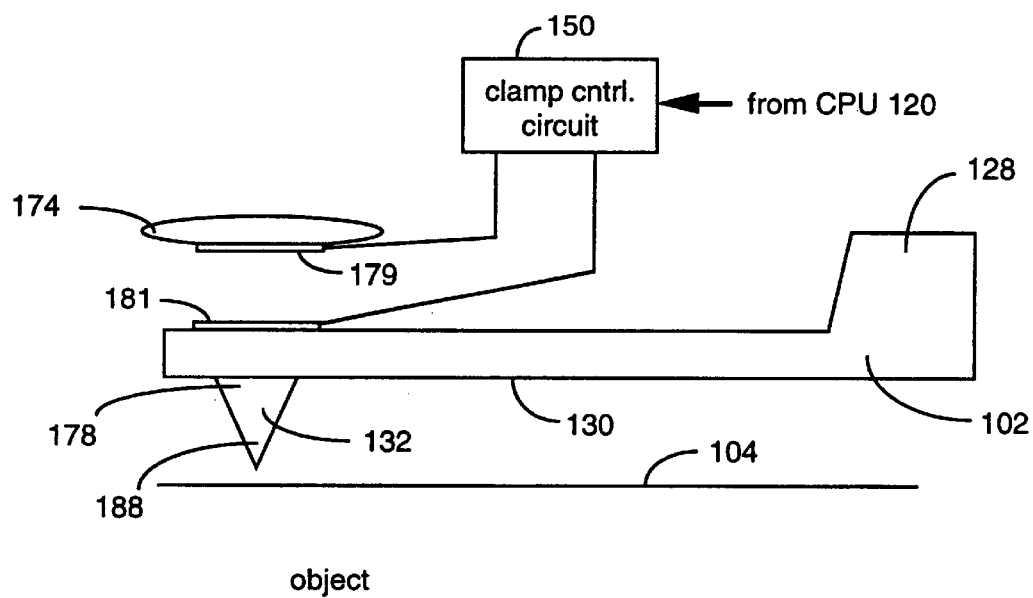
FIG. 5 shows yet another embodiment of a clamping device for holding rigid the cantilever of the scanning probe microscope assembly of FIG. 1 during the STM mode.

Alternatively, optically transparent and conductive coil patterns 179 and 181 are respectively formed on the lower surface of lens 174 and the upper surface of the cantilever 130, as shown in FIG. 5. The coil patterns 179 and 181 are formed from Indium Tin Oxide. In the STM mode, the clamping control circuit 150 applies voltages to the coil patterns 179 and 181 so that their currents are opposite in direction. As a result, an attractive magnetic field is created which immobilizes (i.e., clamps) the cantilever 130. Those skilled in the art will appreciate that one of the coil patterns 179 or 181 may be replaced with a permanent magnet formed with a thin film of samarium cobalt or other permanently magnetizable material. Moreover, this arrangement may also be used to damp, drive, or detect the motion of cantilever depending on which of the modes of operation described herein is being employed by scanning probe microscope 100.

Referring back to FIG. 1, in the STM mode, the scanning control signals generated by the scanning control routine 122 control the XY and Z translators 110 and 112 so that tip 132 is positioned in close proximity to the object 104. Then, scanning control routine 122 generates tunneling control signals provided to the tunneling current measurement circuit 158. In response, the tunneling current measurement circuit 158 generates a voltage signal applied to the tip 132 of probe 102.

Since tip 132 is coated with a conductive layer, a non-optical interaction in the form of a tunneling current is produced between the tip 132 and the object 104. The tunneling current in the object 104 is detected and measured by the tunneling current measurement circuit 158. In response, the tunneling current measurement circuit 158 outputs a tunneling current measurement signal containing data representing the measured tunneling current. The measured tunneling current corresponds to the topography of the object.

Alternatively, those skilled in the art will appreciate that the tunneling current may be kept fixed by changing the position of tip 132 with the Z axis translator 112. The amount of change in position required to keep the tunneling current constant is the measure of topography of the surface.

The tunneling current signal is provided to the CPU 120. The data contained by the signal is analyzed and processed by the STM analysis routine 138 to produce STM image data representing a high magnification (or nanoview) image of the topography of the object 104. The display routine 136 then formats the STM image data, in the way described later, and the CPU 120 provides it to the display monitor 118 for display. The routine 138 is stored in the memory 124 and run on the CPU 120.

Low Magnification Optical Microscopy Mode

Referring again to FIG. 1, scanning probe microscope assembly 100 is configured also to provide conventional or confocal optical microscopy. As is explained later, the optical microscopy mode may occur when the user issues with control terminal 116 a low magnification zoom control signal received by the CPU 120 for a low magnification scan of the object 104. During this scan, the scanning control routine 122 generates scanning control signals outputted by the CPU 120 for controlling the XY translator 110 to position probe 102 over the surface of the object 104 for a low magnification optical microscopy measurement. As will be described later, the low magnification optical microscopy mode is used in conjunction with the high magnification AFM or STM modes and the medium magnification optical microscopy mode (discussed later) to provide a continuous zoom display of an image of object 104 on the display monitor 118.

In order to perform low magnification visible optical microscopy, scanning probe microscope assembly 100 includes a conventional visible optical microscope 160 and visible optical camera 162. The visible light source of the microscope 160 illuminates the object 104 with visible light. The portion of visible light which is within the visible field of view of the microscope 160 and reflected by the object 104 and the probe 102 is then received by the microscope 160. This reflected visible light passes through the beam splitter 166 to the filter of the microscope 160 which removes any non-visible components. The filtered visible light is then focused on the camera 162 by the eyepiece (i.e., focusing lens) of microscope 160. The objective of microscope 160 is chosen to provide a numerical aperture in the range of approximately 0.1–0.2 for low magnification (i.e., macroview of) visible images of the object 104.

The camera 162 then converts the focused visible light into a data signal containing data representing the focused visible light. The data contained by the signal is analyzed and processed by the low magnification optical microscopy analysis routine 139 to produce visible image data representing a low magnification (or macroview) visible image of the topography of the object 104. The display routine 136 then formats the visible image data, in the way described later, and the CPU 120 provides it to the display monitor 118 for display. The routine 139 is stored in the memory 124 and run on the CPU 120.

Medium Magnification Optical Microscopy Mode

The scanning probe microscope assembly 100 of FIG. 1 is further configured to provide medium magnification infrared or visible optical microscopy. The medium magnification microscopy mode may occur when the user issues with control terminal 116 a medium magnification zoom control signal received by the CPU 120 for a medium magnification scan of the object 104, as is explained later. During this scan, the scanning control routine 122 generates scanning control signals outputted by the CPU 120 for controlling the XY translator 110 to position probe 102 over the surface of the object 104 for a medium magnification optical microscopy measurement. As was alluded to earlier, the medium magnification optical microscopy mode is used in conjunction with the high magnification AFM or STM mode and the low magnification optical microscopy mode to provide a continuous zoom display of an image of object 104 on the display monitor 118.

In the case where tip 132 is made of a material, such as silicon, which is opaque to visible light, the scanning control routine 122 generates control signals for controlling the light source 180 to provide a wide beam of infrared light. The light source 180 of the spectrophotometer 182 is configured so that the wavelength (i.e., frequency) and beam size of the light that it provides may be varied in ways well known to those skilled in the art. In the preferred embodiment, this light source 180 is variable in wavelength over the range of approximately 6 microns to 200 nm and has a beam size variation ratio of approximately 1000 to 1 so that the beam can be as made as narrow as the base of the tip 132 (down to 1 micron) and as wide as the largest objective in the system (up to 2 cm).

The wide beam of infrared light is directed by the beam splitters 186 and 188 to the beam splitter 166. The beam splitter 166 reflects (i.e., directs) the wide beam of infrared light to the lens system 174.

Figure 6:
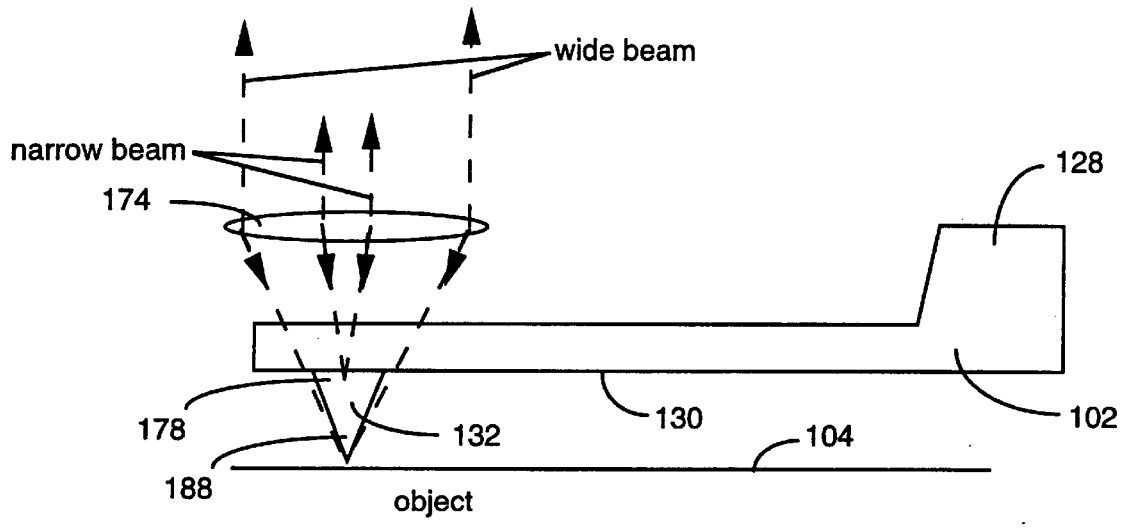
FIG. 6 shows the operation of the lens of FIG. 2c or 3c.

As shown in FIG. 6, the lens system 174 is disposed over the portion of the cantilever 130 connected to the base 128 of the tip 132. For the embodiments of FIGS. 2a and 2b, the lens system 174 is held and supported by the thin lens system support 176, as shown in FIG. 2c. The lens system support 176 is transparent to visible light, is connected to the base 128 of the probe 102, and holds and supports the lens system 174. For ease of illustration, FIG. 2c does not show the clamping arm 140 shown in FIGS. 2a and 2b.

The lens system 174 may be a standard objective arrangement of one or more lenses to form an appropriate tube length or provide the preferred infinity corrected tube length in a manner well known to lens designers. A two lens system may be made by providing a mounting barrel with a partial or complete hole in the thin support structure. Moreover, as those skilled in the art will appreciate, lens system 174 may be a fresnel lens arrangement constructed similar to the fresnel lens 250 shown in FIGS. 11a and 11b.

The lens system support 176 is transparent to visible light and may extend across the entire visible field of the visible optical microscope 160. It may include a cutoff filter such that only visible light may pass through it while infrared light is blocked except in a central area within the lens system 174 where it acts like a field stop (part of standard objective lens design practice and well known in the art) to eliminate extraneous light which would lower contrast in the medium magnification optical mode.

The lens system support 176 may also be an electro-optically adjustable iris, mechanical iris, optically enabled iris, such as a glass assembly made from glass doped everywhere except over lens system 174 which becomes opaque on exposure to UV light from the light source 180, and may be used as a field stop. This is true even when lens system 174 is a fresnel lens arrangement such as that shown in FIGS. 12a and 12b.

For the embodiments of FIGS. 3a, 3b, 4a, 4b, and 5, the lens system 174 and the clamping structure 141 are shown in FIG. 3c. The clamping structure 141 serves as a support shelf for lens system 174.

Referring again to FIG. 6, lens system 174 is spaced from the cantilever 130 such that it has a focal length in focus with the surface of the object (and also the sharp end 188 of the tip 132) for the wide beam of infrared light 167 received from the beam splitter 166. The focal length is chosen so that lens system 174 has a numerical aperture in the range of approximately 0.7 to 0.9 to provide medium magnification (i.e., microview of) images of the object 104. Typically, the lens system 174 is disposed above the cantilever 130 in the range of approximately 40 to 4000 microns.

Moreover, lens system 174 occupies only a small area of the visible light field of view of the microscope 160. In particular, lens system 174 has a diameter substantially smaller than the diameter of the objective lens of the microscope 160 shown in FIG. 1 but large enough to allow the wide beam of infrared light to be focused at the surface of the object 104, as shown in FIG. 6. The diameter of lens system 174 must be appropriate for the size of the cantilever 130 and is typically less then 2 mm and is approximately in the range of 100 to 500 microns.

Moreover, FIG. 1 shows the optical path of the cantilever deflection optics 134 traveling through the lens system support 176 but not the lens system 174. However, those skilled in the art will appreciate that the optics 134 may be arranged to have an optical path that travels through the lens system 174.

The wide beam of infrared light focused by the lens system 174 at the surface of the object 104 is reflected by the object 104 back to the lens system 174, as shown in FIG. 6. Referring to FIG. 1, the beam splitters 166 and 188 direct the reflected infrared light to the optics 168. The filter of the optics 168 allows only the wide beam of reflected infrared light to pass which is then focused by the eyepiece (i.e., focusing lens) of the optics 168 on the camera 178.

The camera 178 converts the focused infrared light into an infrared data signal containing data representing the focused infrared light. The data contained by the signal is analyzed and processed by the medium magnification optical microscopy analysis routine 141 to produce infrared image data representing a medium magnification (or microview) image of the topography of the object 104. The display routine 136 then formats the infrared image data, in the way described later, and the CPU 120 provides it to the display monitor 118 for display. The routine 141 is stored in the memory 124 and run on the CPU 120.

Alternatively, when the tip 132 is made of a material, such as silicon nitride, which is transparent to visible light, then lens system 174 may be configured and disposed over the tip 132 so that it has a focal length in focus with the surface of the object (and also the sharp end 188 of the tip 132) for a portion 165 of the visible light 164 provided by the visible light source of the microscope 160. Again, the focal length is chosen so that lens system 174 has a numerical aperture in the range of approximately 0.7 to 0.9 to provide medium magnification (i.e., microview of) images of the object 104.

The portion 165 of visible light focused by the lens system 174 at the surface of the object 104 is reflected by the object 104 back to the lens system 174. From there, it is directed by the beam splitters 166 and 188 to the optics 168. In this case, the filter of the optics 168 allows only the visible light portion to pass through and be focused by the eyepiece of the optics 168 on the camera 178.

The camera 178 converts the focused visible light 165 into a visible data signal containing data representing the focused visible light. Similar to above, the medium magnification optical microscopy analysis routine 141 produces medium magnification visible image data representing a medium magnification (or microview) image of the topography of the object 104 which is then formatted by the display routine 136 and displayed on the display monitor 118.

Near-Field Spectrophotometry Mode

Referring to FIG. 1, scanning probe microscope assembly 100 is configured also to perform near-field spectrophotometry. As explained later, the near-field spectrophotometry mode may occur when the user selects this mode with the control terminal 116 and issues with control terminal 116 the high magnification zoom control signal described earlier. The near-field spectrophotometric measurements may be made in conjunction with AFM and STM measurements during the high magnification scan.

When a near-field spectrophotometric measurement is to be made, scanning control routine 122 will generate scanning control signals outputted by the CPU 120 for controlling the XY and Z translators 110 and 112 to position tip 132 in close proximity to the object 104 for making near-field spectrophotometric measurements. In the preferred embodiment, the sharp end 188 of the tip 132 is placed from the object 104 no further then approximately half of the wavelength of the light provided by the light source 180 for the near-field spectrophotometric mode.

Additionally, scanning control routine 122 generates control signals to control light source 180 to provide a narrow beam of infrared or visible light 185 which is transparent to the probe 102 and the lens system 174. This is done at a variety of chopping frequencies to enable the photodetectors 192 and 194 of the spectrophotometer to discriminate between the detected optical energy due to excitation by the light 185 and detected background energy through lock-in amplification and other noise rejection and amplification methods well known to those in the art. As a result, spectrophotometer 182 may make absorption, Raman, second harmonic, fluorescence, and other well known spectrophotometric measurements of the object 104.

The mechanically rotatable plane polarizer 184 is held stationary in the near-field spectrophotometry mode. The light 185 from the light source 180 is plane polarized by the polarizer 184, passes through the beam splitters 186 and 188, and is directed by the mirror 172 to the lens system 174.

The light 185 is focused by the lens system 174 within the base 178 of the tip 132, as shown in FIG. 6. The tip 132 acts similar to an antenna coupled to a waveguide such that the light 185 focused within the base 178 propagates through the tip 132 and is emitted at the sharp end 188 of the tip 132. The emitted light 185 optically interacts with the object 104. Since the tip 132 acts as an antenna, the sharp end 188 of the tip 132 captures the resulting light due to the optical interaction of the emitted light with the object 104. This light propagates back through the tip 132 to the lens system 174.

As was just alluded to, tip 132 acts similar to an antenna. This, the propagation in, emission of, and capture of energy in a pyramid shaped antenna is analogous to that of tip 132 when shaped as a cone or tetrahedral. The propagation, emission, and capture of energy in a pyramid shaped antenna is described in *The Radiation Patterns of Dielectric Rods-Experiment and Theory*, by R. B. Watson and C. W. Horton, Journal of Applied Physics, volume 19, pg. 661 (1948) and is expressly incorporated by reference herein.

Specifically, the electrical and magnetic fields at the base 178 of tip 132 are analogous to the following equations which define the electrical and magnetic fields at the base of a pyramid shaped antenna:

$$E_{0,1} = x \cos(\pi y_1/b) \exp(-j(\omega t - k'z_1)),$$

$$H_{0,1} = [y(k'/w\mu) \cos(\pi y_1/b) + z(\pi/jw\mu b) \sin(\pi y_1/b)] \exp(-j(wt-k$$

where a and b represent the size of the sides of the base of the pyramid shaped antenna, k represents the wave number in a vacuum, and k' represents the wave number in the material of a waveguide connected to the antenna.

The method employed by Watson and Horton prescribes magnetic currents on the two electrical field plane sides of the pyramid shaped antenna and electric currents on the two magnetic field plane sides. The emitted and captured optical energy is then found by applying a Fresnel-Huygens method to obtain the radiation fields produced by these currents. Adopting spherical geometry, with the z axis corresponding to $\theta=0$, the following fields are obtained:

$$E_r = 0,$$

$$E_\theta = (jk \cos\theta) P_1(\theta, \phi),$$

$$E_\phi = (-jk \sin\phi \cos\theta) P_1(\theta, \phi).$$

where $$P_1(\theta, \phi) = M_0 \cos[(ka/2)\sin\theta\cos\phi] \cdot I_1 \cdot I_2$$

$$I_1 = 2\frac{b}{\pi} \frac{(\pi/2)^2 \cos((kb/2)\sin\theta\sin\phi)}{(\pi/2)^2 - ((kb/2)\sin\theta\sin\phi)^2}$$

-continued $$I_2 = \frac{1}{2k}(A - jB),$$

$$A = \frac{1}{n - \cos\theta}[1 - \cos[(n + \cos\theta)kl]] + \frac{1}{n + \cos\theta}[1 - \cos[(n + \cos\theta)kl]]$$

$$B = \frac{\sin[(n - \cos\theta)kl]}{n - \cos\theta} - \frac{\sin[(n + \cos\theta)kl]}{n + \cos\theta}$$

Here n=k/k' and l is the length of the pyramid shaped antenna in the z direction.

Figure 7A:
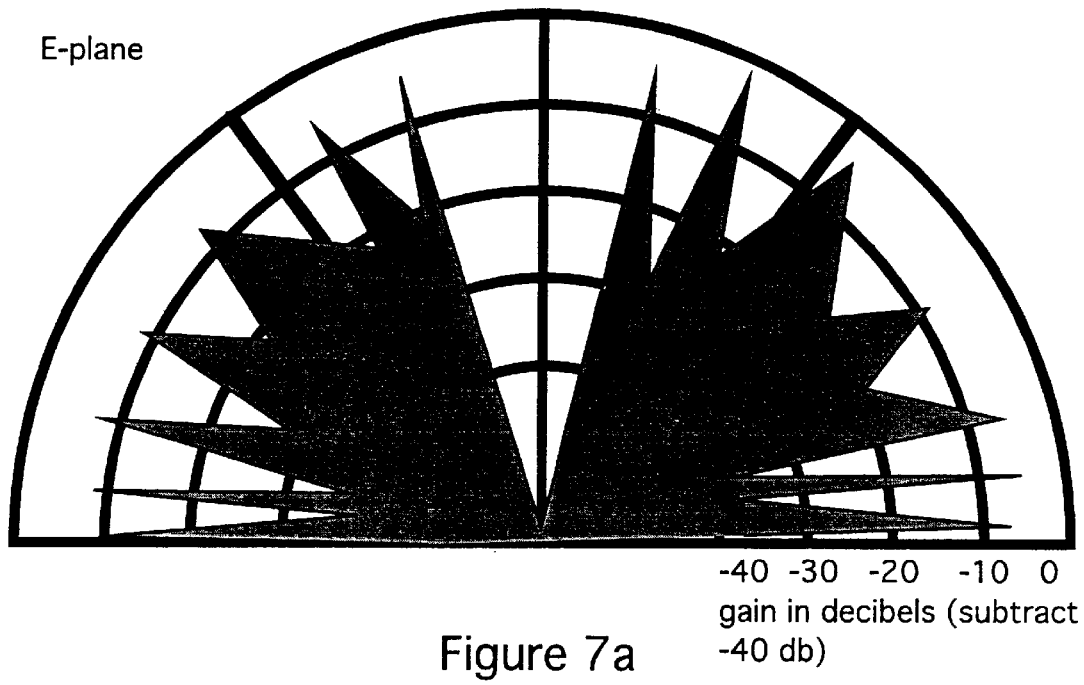
FIGS. 7a and 7b provide electrical field plane and magnetic field plane polar plots of optical energy emissions by the tip of the scanning probe microscope assembly of FIG. 1.
Figure 7B:
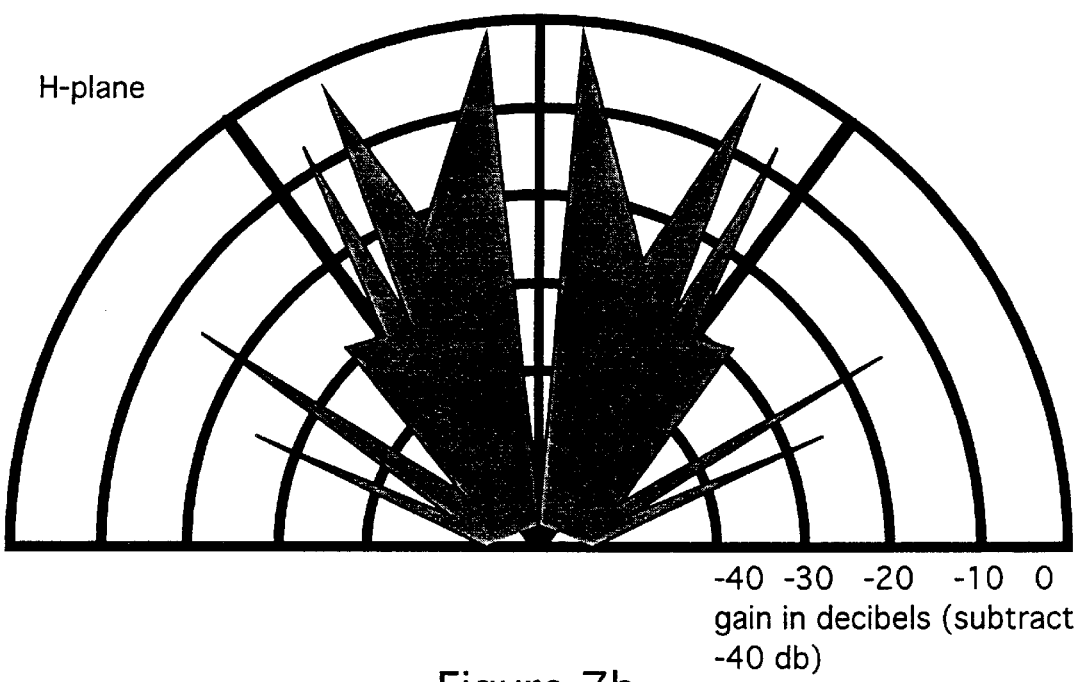

It is clear from the foregoing discussion, that the propagation, emission, and capture of energy described by these equations is analogous to that which occurs in tip 132. FIGS. 7a and 7b provide electrical field plane and magnetic field plane polar plots of optical energy emissions by tip 132 in accordance with the above equations.

Referring again to FIG. 1, from the lens system 174, the captured light 185 is directed by the mirror 166 through the beam splitters 188 and 186 to the monochromator 190. In the preferred embodiment, the monochromator 190 is conventionally configured to separate the captured light into an array of its constituent wavelengths. The photodetector 192 includes an array of photodiodes or photomultipliers for detecting emissions at the various wavelengths. Alternatively, the monochromator 190 may be conventionally configured to sequentially separate the wavelengths of the captured light and the photodetector 192 may be conventionally configured to sequentially scan the spectrum of wavelengths.

The photodetector 192 converts the detected optical energy (i.e., detected wavelengths) into a detection signal containing data representing the detected optical energy. The data contained by the signal is analyzed and processed by the near-field spectrophotometry analysis routine 143 to produce data representing information on the composition of the object 104. Depending on the particular wavelength of the light 185 provided by the light source 180, the optical interaction between the tip 132 and the object may involve reflection, absorption, photoemission (including fluorescence, Raman, and second harmonic), and/or other types of well known interactions.

As was indicated earlier, the scanning control routine 122 generates control signals for varying the wavelength of the light provided by the light source 180. As a result, the above described interactions may be detected by the photodetector 192 and analyzed by the analysis routine 143 to produce data representing information on the composition of the object 104. The data is then formatted for display, in the way described later, by the display routine 136 and provided to the display monitor 119 for display of this information.

Alternatively, or in conjunction with the near-field spectrophotometric arrangement described above, scanning probe microscope assembly 100 of FIG. 1 may also perform near-field spectrophotometry by detecting light energy from the near-field with the photodetector 194 at a distance which is many wavelengths away from the tip 132. In this arrangement, optical interaction between tip 132 and the object 104 is induced in the same way as was described earlier. However, the resulting photoemissive energy (such as fluorescence, Raman, and second harmonic) is detected by the photodetector 194 after the monochromator 196 has separated the photoemissive light into its constituent wavelengths. As with the monochromator 190, the monochromator 196 is preferably configured to separate the photoemissive light into an array of its constituent wavelengths and the photodetector 194 includes an array of photodiodes or photomultipliers for detecting the array of wavelengths.

Photodetector 194 converts the detected optical energy into a detection signal containing data representing the detected optical energy. The data contained by the detection signal is provided to the CPU 120 and analyzed and processed by the near-field spectrophotometry analysis routine 147 to produce data representing information on the composition of the object 104. This data is formatted by the display routine 136, in the way described later, and provided to the display monitor 119 for display of the information.

Near-Field Optical Microscopy Mode

Turning again to FIG. 1, scanning probe microscope assembly 100 is also configured to perform near-field optical microscopy to define deep surface features of the object 104 which cannot be detected through the AFM or STM mode. Like the near-field spectrophotometry mode, the near-field optical microscopy mode may occur when the user selects this mode with the control terminal 116 and issues with control terminal 116 the high magnification zoom control signal described earlier. The near-field optical microscopy measurements may be made in conjunction with AFM, STM, and spectrophotometric measurements during the high magnification scan.

As was just alluded to, this mode is used when the AFM or STM measurements indicate that tip 132 is not directly over a structure of the object 104 and is instead directly over a deep surface feature, such as a pit, wall, or projection. When this occurs, optical interaction between tip 132 and the object 104 is induced in the same way as was described earlier for the near-field spectrophotometry mode except that scanning control routine 122 issues a control signal for controlling the rotatable plane polarizer 184 to rotate during this mode. As a result, the light is rotationally plane polarized (i.e., the polarization state of the light provided by the light source 180 is continuously changed) during the near-field optical mode.

The optical energy pattern detected by the photodetector 192 or 194 during this rotation is recorded by the near-field optical analysis routine 151. The routine 151 then compares the recorded optical energy pattern with predefined optical energy patterns stored in the data base 198 of the memory 124 which correspond to various types of deep surface features. This comparison is made in order to determine what is directly underneath or near tip 132. The analysis routine 151 then generates image data representing an image of the determined deep surface feature and the display routine 136 formats the data for display of this image on the display monitor 118.

Moreover, this type of near-field microscopy may be used to examine tip 132 in a tip testing mode. This is done by placing tip 132 over a uniform and already defined hole in an object. By comparing the optical energy pattern detected by the photodetector 192 or 194 with a predefined optical energy pattern stored in the data base 198 for a non-defective tip, the analysis routine 151 can determine whether tip 132 is defective or not.

Alternatively, rather than utilizing the rotatable linear polarizer 184, those skilled in the art will recognize that scanning probe microscope assembly 100 may be configured so that the plane polarizer 184 is stationary and probe 102 is rotated by rotating the Z translator 112 in a conventional manner during this mode. Alternatively, object 104 may be rotated by rotating the XY translator 110 in a conventional manner during this mode. As a result, an optical energy pattern detected by the photodetector 192 or 194 during such rotation can be compared with predefined optical energy patterns stored in the data base 198.

Hardness Testing Mode

The scanning probe microscope assembly 100 of FIG. 1 is also configured to perform hardness testing of object 104. The hardness testing mode may also occur when the user selects this mode with the control terminal 116 and issues with control terminal 116 the high magnification zoom control signal. The hardness testing measurements may also be made in conjunction with AFM, STM, spectrophotometric, and near-field optical measurements during the high magnification scan.

In the hardness testing mode, the scanning control routine 122 controls the making of a near-field spectrophotometric measurement in the way described earlier at a particular location of the object 104. A detection signal is provided to the CPU 120 by the photodetector 192 or 194 and the hardness testing analysis routine 195 records in the data base 198 the data of the detection signal representing the optical energy detected by the photodetector 192 or 194. The routine 195 is stored in the memory 124 and run on the CPU 120.

Then, the scanning control routine 122 generates scanning control signals for controlling the Z translator 112 so that tip 132 directly contacts, penetrates, and deforms the surface of the object 104 with a known force at the same location where the near-field spectrophotometric measurement was just made. While the tip 132 penetrates the surface of the object, scanning control routine 122 then controls the making of another near-field spectrophotometric measurement at the same location.

The data contained in the resulting detection signal provided by the photodetector 192 or 194, together with the earlier recorded data, is analyzed and processed by the hardness testing analysis routine 195 to produce data representing information on the hardness of the object 104. This is done by determining the proportionate change in the detected optical energy between the two measurements which provides a measure of the depth of penetration of tip 132. The depth of penetration in turn is a measure of the local binding strength (i.e., hardness) of the object 104. In bulk materials, this measure reflects local changes such as crystal dislocations, etc . . . .In patterned materials, such as semiconductors, this measure provides subsurface structural information. This data is formatted by the display routine 136, in the way described later, and provided to the display monitor 119 for display of the hardness information.

Alternatively, the hardness testing mode may involve STM measurements. In this variation, the scanning control routine 122 controls the tunneling current measurement circuit 158 to make a conductivity measurement for object 104 at a particular location of the object 104 in a similar way to that described earlier for STM measurements. The data in the conductivity measurement signal representing the conductivity measured by the circuit 158 is recorded in the data base 198 by the hardness testing analysis routine 195.

Similar to before, the scanning control routine 122 generates scanning control signals for controlling the Z translator 112 to make the tip 132 directly contact, penetrate, and deform the surface of the object 104 with a known force at the same location. While the tip 132 penetrates the surface of the object 104, scanning control routine 122 then controls the making of conductivity measurements of object 104 at the same location.

The data in the conductivity signal over the period before and during the penetration is recorded, analyzed, and processed by the hardness testing analysis routine 195 to produce data representing information on the hardness of the object 104. In this case, the measured change in conductivity over the period before and during penetration is a measure of the depth of penetration of tip 132 and in turn a measure of the hardness of the object 104. The data produced by the routine 195 is formatted by the display routine 136 and provided to the display monitor 119 for display of the hardness information.

Additionally, the actual deflection or motion of the tip as measured by the optics 134 and the deflection measurement circuit 136 can be used by the hardness testing routine 195 in conjunction with the known force to provide a measure of the hardness of the surface. Like in the earlier described hardness testing embodiments, the data produced by the routine 195 is formatted by the display routine 136 and provided to the display monitor 119 for display of the hardness information.

Probe and Lens Composition

In order to provide all of the foregoing modalities associated with the embodiment of FIG. 1, the probe 102 in the embodiment of FIGS. 2a–2c and the embodiment of FIGS. 3a–3c is formed from a wafer of silicon, silicon nitride, or some other material which is transparent to visible or infrared light. Specifically, in the case where infrared light is used for the medium magnification optical microscopy, the near-field optical microscopy, and the spectrophotometry modes, the probe is formed from a material, such as silicon, which is transparent to infrared light. And, in the case where visible light is used for these modes, the probe is formed from a material, such as silicon nitride, which is transparent to visible light.

The base 128, cantilever 130, tip 132, and clamping arm 140 or clamping structure 141 of probe 102 are etched from the wafer using conventional techniques known to those skilled in the art.

The lens system 174 may also be formed from silicon, silicon nitride, or some other material transparent to infrared or visible light depending on whether infrared or visible light is used for the modes just described above. Similarly, depending on whether infrared or visible light is used for these modes, the lens system support 176 of the embodiment of FIGS. 2a–2c is made of silicon, glass, or some other material transparent to infrared or visible light.

Figure 8A:
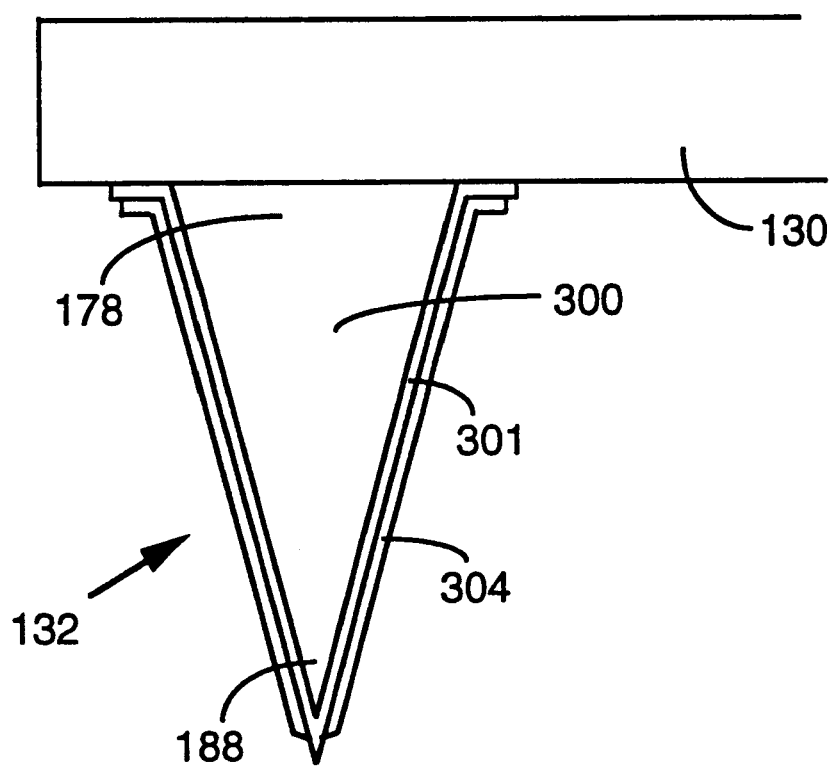
FIGS. 8a–8d show various embodiments of the tip of the scanning probe microscope assembly of FIG. 1.

As shown in FIG. 8a, the core material (silicon, silicon nitride, or other material) 300 of the tip 132 may be coated with an obdurate rigid material 301, such as diamond, tungsten, silicon carbide, or carbon nitride, to increase tip life, as shown in FIG. 8a. The obdurate coating 301 may have a thickness in the range of approximately 5 Angstroms to 1 micron.

To allow operation in the STM mode and/or contain light energy within the tip 132, the tip 132 may be coated using conventional techniques with a thin layer 304 of a conductive material, such as aluminum, tungsten, or gold. This layer 308 is formed over the core material 300 and any obdurate coating 301 at a thickness in the range of approximately 1 Angstrom to 1 micron.

A small portion of the conductive layer 304 is removed or rubbed off at the sharp end 188 of the tip 132 using conventional techniques to at least the point where the conductive layer 304 is no longer opaque to light propagating through the tip 132. Furthermore, the conductive coating 304 is removed or rubbed off only so that the conductive coating 304 ends approximately 5 to 10 nm from the point of the sharp end 188. As a result, an aperture having a diameter in the range of approximately 5 to 100 nm is formed at the sharp end 188.

Figure 8B:
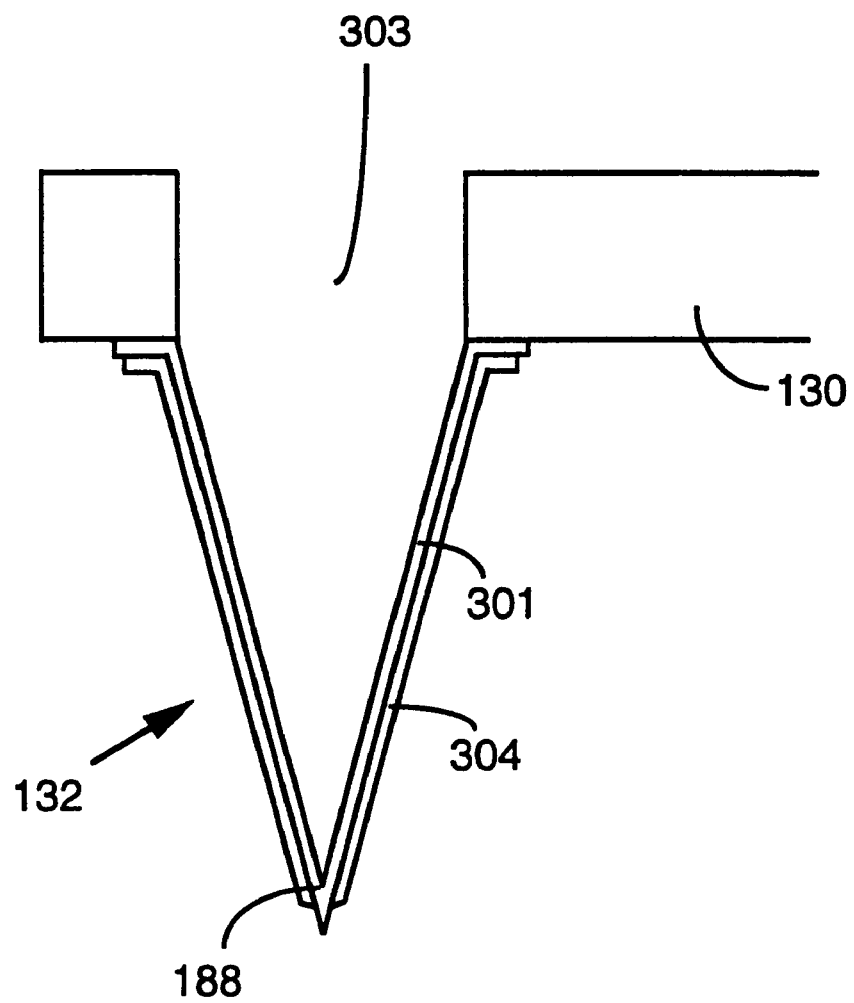
Figure 8C:
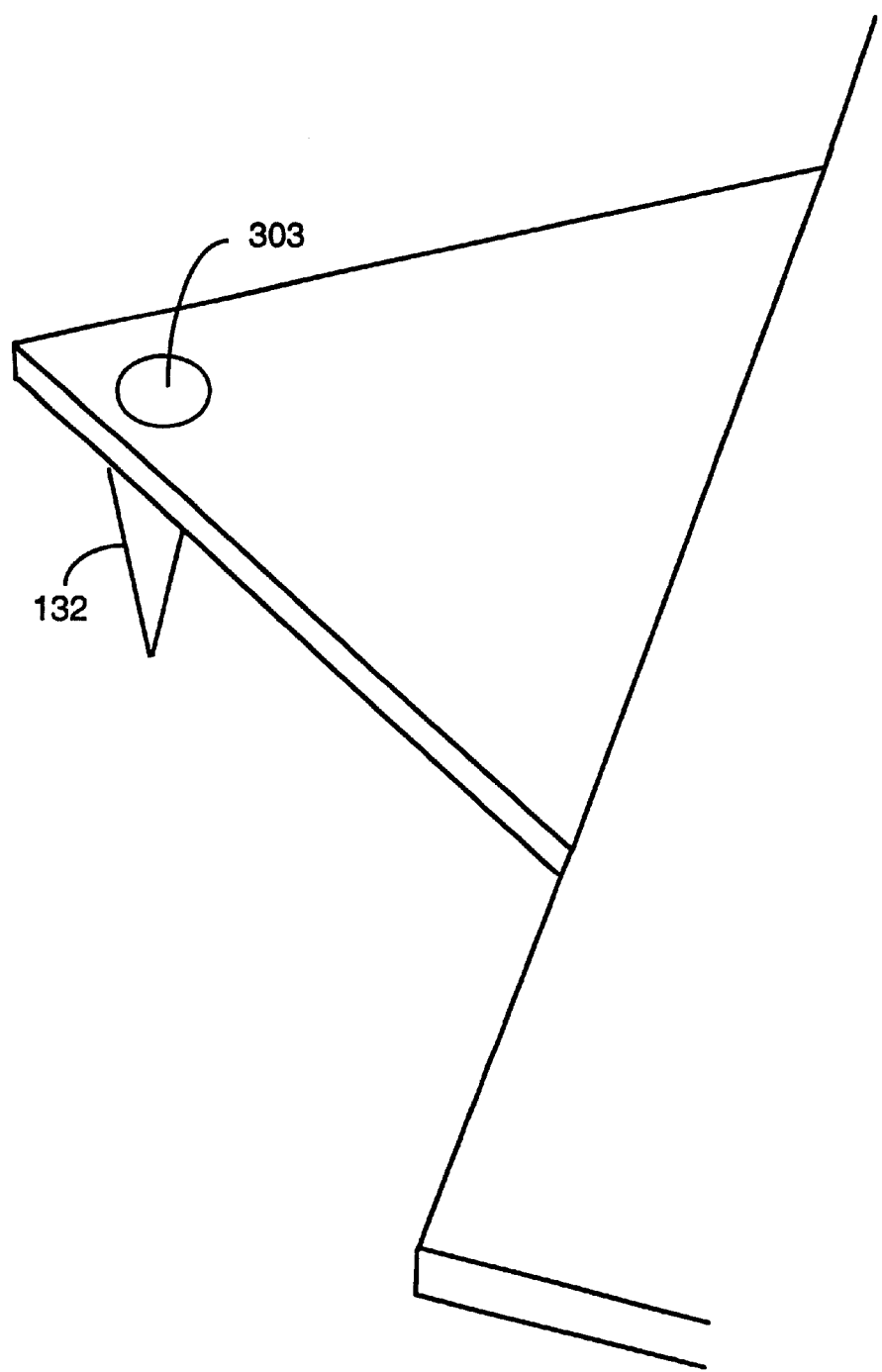

Alternatively, referring to FIGS. 8b and 8c, the core material 300 of the tip 132 and the core material 300 of the cantilever 130 over the tip 132 (shown in FIG. 8a) are etched away using conventional techniques to leave a hole 303 in the cantilever 130 and only the obdurate coating 301 and the conductive coating 304 as the tip 132. As in the tip 132 of FIG. 8a, the conductive coating 304 is removed or rubbed off from the sharp end 188 of the tip 132 to form an aperture near the sharp end 188. In operation, this tip 132 is substantially transparent (in the case of diamond) to an extremely broad range of wavelengths (0.1 to 20 microns).

Furthermore, if the obdurate coating 301 of FIGS. 8a–8c is a silicon carbide or silicon nitride coating, it may be doped using conventional techniques so as to be conductive. In this case, the conductive layer 304 would be omitted.

In the case where the obdurate coating 301 of FIGS. 8a–8c is a layer of diamond, the diamond crystals are grown so as to be oriented normal to the surface of the tip 132. This is done in the following manner.

First the wafer containing the probe 102 is placed in a vacuum are deposition chamber containing carbon. A mask is placed over the probe 102 so that only the tip 132 and the area of the cantilever 130 around the base 178 of the tip 132 are exposed. At a pressure of approximately $1 \times 10^{-7}$ to $1 \times 10^{-11}$, the carbon is heated to a temperature of approximately 2100 to 3000° C. The carbon condenses on the surface of the core material 300 or an overlying tungsten, silicon carbide or silicon nitride layer.

The probe 102 is then placed in a methane hydrogen atmosphere for chemical vapor deposition (CVD) growth of the diamond layer 301 on the surface of the core material 300. The condensed carbon acts as a seed such that the diamond layer 301 grown is a layer of polycrystalline diamond oriented normal to the surface of the core material 300 or overlying layer.

In the case where the obdurate layer 301 is carbon nitride, the same seeding process as was described above is used. Then the probe 102 is placed in an atmosphere of monatomic nitrogen. The monatomic nitrogen is obtained by passing nitrogen gas through a hollow tungsten heater consisting of a hollow tungsten structure through which an electric current is passed. The tungsten heater is maintained at a temperature of 2100 to 3000° C. In one embodiment the tungsten heater also includes a quantity of carbon sufficient to combine chemically to form the carbon nitride layer 301 on the carbon condensation at the cool core material 300 surface (800° C.). The process begins without introducing nitrogen gas. After a few atoms of carbon are deposited, the nitrogen gas is introduced into the tungsten electrode and deposition and growth of the polycrystalline carbon nitride layer 301 is initiated.

Figure 8D:
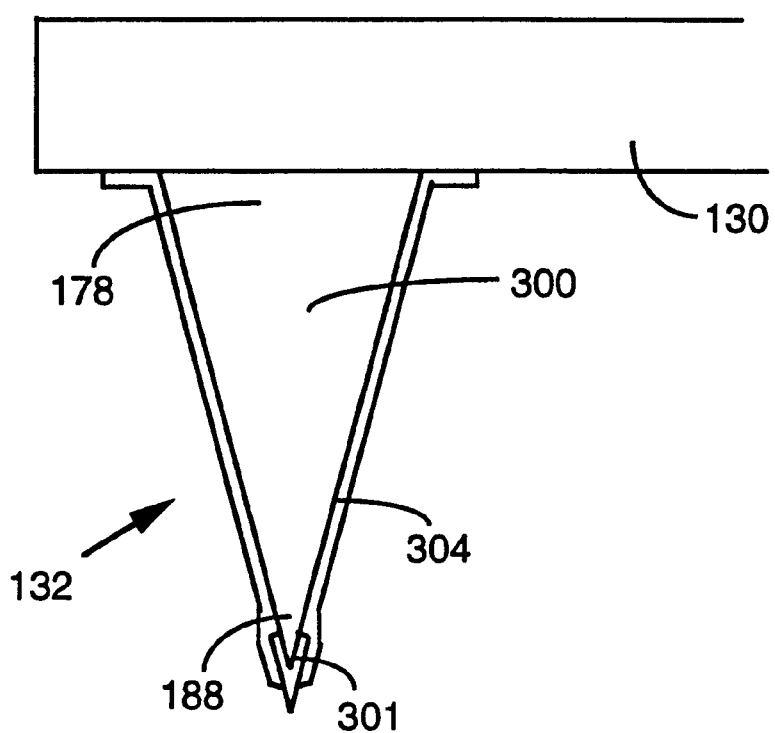

FIG. 8d shows a tip 132 with an obdurate diamond layer 301 over the core material 300 just at the sharp end 188. As in the tips 132 of FIGS. 8a–8c, the conductive coating 304 is removed or rubbed off from the sharp end 188 of the tip 132 to form an aperture at the sharp end 188.

The core material 300 or an overlying tungsten, silicon carbide or silicon nitride layer at the sharp end 188 is pushed into or rubbed on a surface containing fine grain diamond (such as a lap or polycrystalline diamond coated surface). The sharp end 188 picks up a seed crystals of diamond. The probe 102 is then placed in a CVD environment for growth of the polycrystalline diamond layer 301 at the seed sites around the sharp end 188.

Scanning Sequence

Figure 9:
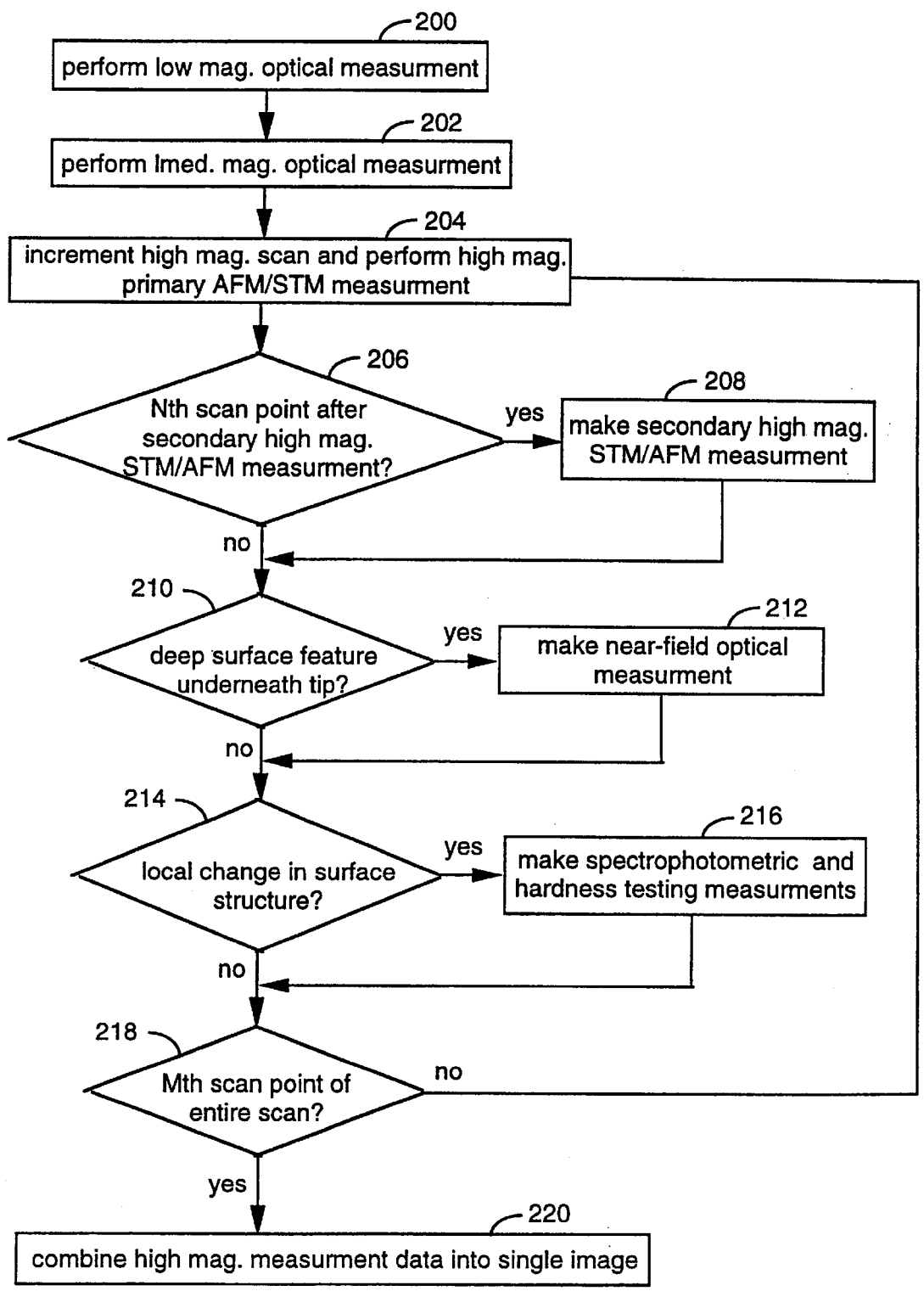
FIG. 9 shows a typical scanning sequence flow of operation of the scanning probe microscope assembly of FIG. 1.

FIG. 9 shows the scanning sequence controlled by the scanning control routine 122.

Initially, the user issues with the control terminal 116 a low magnification zoom control signal for directing a low magnification visible optical microscopy scan of the object 104. In response, the scanning control routine 122 controls the XY translator 110 to position the object in the area specified by the low magnification zoom control signal and then low magnification visible optical microscopy measurements are made in these areas in the way described earlier (block 200). This is done in order that the user may find an area of the object 104 to zoom in on for closer inspection with some of the other modes described earlier.

Once an area for inspection is located with the low magnification visible optical microscopy scan, then the user issues with control terminal 116 a medium magnification zoom control signal for directing a medium magnification optical microscopy scan of the object 104 in this area. The scanning control routine 122 controls the XY translator 110 to position the tip 132 over the object 104 in the area specified by the zoom control signal and then medium magnification optical microscopy measurements are made in this area in the way described earlier (block 202). This is done to find a smaller area to zoom in on for even closer inspection.

After this smaller inspection area is located, the user issues with control terminal 116 a high magnification zoom control signal for directing a high magnification scan of the object 104 in this area. In doing so, the scanning control routine 122 controls the XY translator 110 so that the tip 132 is sequentially positioned at numerous scan points over the object 104 during the scan.

When the AFM mode has been selected as the primary high magnification mode by the user with the control terminal 116, a flag is set in the data base 198 indicating this. In response to this flag, the scanning control routine 122 directs the Z translator 110 to position tip 132 over the object 104 for an AFM measurement at each scan point in the way described earlier (block 206). The data processed by the AFM analysis routine 137 representing these AFM measurements is then recorded in the data base 198.

Alternatively, when object 104 is a conductive material, the user may select the STM mode as the primary high magnification mode. In this case, the scanning control routine 122, in response to a flag stored in the data base 198 indicating that the STM mode is the primary high magnification mode, directs the Z translator 110 to position tip 132 over the object 104 at each scan point for an STM measurement at each scan point (block 206). These STM measurements are made in the way described earlier and the combined data representing them is processed by the STM analysis routine 138 and recorded in the data base 198. When combined, the recorded data provides the basic high magnification image data of object 104.

After a primary high magnification measurement is made at a scan point, the scanning control routine 122 determines whether to make at this same scan point a secondary high magnification STM measurement (in the case where the primary high magnification mode is the AFM mode) or AFM measurement (in the case where the primary high magnification mode is the STM mode). The scanning control routine 122 accomplishes this by determining if a predefined number N of scan points have occurred since the last secondary STM measurement (in the case where the primary high magnification mode is the AFM mode) or the last secondary AFM measurement (in the case where the primary high magnification mode is the STM mode) (decision block 208). This predefined number N may be selected by the user with the control terminal 116.

If scanning control routine 122 determines that the scan has been incremented by N scan points since the last secondary high magnification STM or AFM measurement, then it controls the making of such a measurement in the way described earlier (block 210). The data representing this measurement is processed by the STM or AFM analysis routines 137 or 138 and then stored in the data base 198. This data provides additional information or image data on local variations of composition or conductivity at the current scan point.

After the secondary measurement has been made at the current scan point, or after scanning control routine 122 determines that such a measurement should not be made at this scan point, it then determines based on the primary high magnification AFM or STM measurement whether a deep surface feature is immediately under the tip 132 if it already has not determined that an anomaly exists at the current scan point (decision block 212). Similar to the way in which an anomaly is detected, this is done by analyzing the data contained in the signal received from the cantilever deflection measurement circuit 135 (when the AFM mode is the primary magnification mode) or the tunneling current measurement circuit 158 (when the STM mode is the primary magnification mode) and comparing it with predefined data stored in memory 124 corresponding to a deep surface feature.

If scanning control routine 122 determines that the received data does not compare with the stored data, then it has determined that a structure and not a deep surface feature is directly underneath tip 132. In this case, a near-field optical measurement is not made.

However, when the received data does compare to the stored data, then scanning control routine 122 has determined that a deep surface feature is underneath tip 132 at the current scan point. In this case, the scanning control routine 122 then controls the making of a near-field optical microscopy measurement at this scan point in the way described earlier (block 214). The data produced by the near-field optical analysis routine 151 provides image data identifying the deep surface structure and is recorded in the data base 198.

After a near-field optical measurement has been made at the current scan point, or if it is determined that such a measurement is not to be made, then the scanning routine 122 determines whether a junction of surface structures or local change in surface structure exists at the current scan point (decision block 216). Similar to the deep surface feature determination described above, scanning control routine 122 determines this by analyzing the data contained in the signal received from the cantilever deflection measurement circuit 135 (when the AFM mode is the primary magnification mode) or the tunneling current measurement circuit 158 (when the STM mode is the primary magnification mode) and comparing it with predefined data stored in memory 124 corresponding to known types of structure junctions to determine if a structure junction is directly underneath tip 132.

If scanning control routine 122 determines that a junction of structures or a local change in structure is directly underneath tip 132, then it controls performance of a near-field spectrophotometric measurement, and/or a hardness testing measurement in the ways described earlier (block 218). The data produced by the analysis routines 143, 151, and 195 provides even more information or image data on local variations of composition at the current scan point and is recorded in the data base 198.

After a near-field spectrophotometric measurement, and/ or a hardness testing measurement is made, or if scanning control routine 122 determines that a junction of structures or a local variation in structure is under tip 132 at the current scan point, then the scanning control routine 122 determines if the scan has been completed. This is done by determining if the current scan point is the last scan point of a predefined number of scan points M selected for the entire scan by the user with the control terminal 116.

If the current scan point is not the Mth scan point, then the scan is incremented to the next scan point and the above process is repeated until the Mth scan point is reached. However, if the current scan point is the Mth scan point, then the display routine 136 combines the data processed by the routines 137, 138, 151, 143, and 195 into a single high magnification image of the object in the way described later (block 220).

As one skilled in the art will appreciate, the user can increase the overall scan time by selectively setting flags in the data base 198 indicating which of the above described measurements should not be made during the scan. In response, the scanning control routine 122 will not control the performance of these types of measurements.

Moreover, those skilled in the art will appreciate that the scanning control routine 122 can be modified to make different types of measurements for different types of conditions and materials being inspected.

For example, the near-field optical mode, the near-field spectrophotometry mode, or the hardness testing mode may be made the primary measurement mode.

Or, scanning control routine 122 may also determine that secondary STM or AFM, near-field optical, spectrophotometric, or hardness testing measurements should be made if, based on the primary high magnification AFM or STM measurement, scanning control routine 122 determines that an anomaly exists at a current scan point. This is done similarly to the deep surface feature determination. Specifically, scanning control routine 122 analyzes the data contained in the signal received from the cantilever deflection measurement circuit 135 (when the AFM mode is the primary magnification mode) or the tunneling current measurement circuit 158 (when the STM mode is the primary magnification mode) and compares it with predefined data stored in memory 124 corresponding to known types of structures and surface features to determine if an anomaly is directly underneath tip 132.

Moreover, the criterion for making the various types of measurements described above may be based instead on the planarity of the specimen. Thus, the scanning control routine 122 would control the making of measurements in the magnification and measurement mode appropriate to the region under the tip 132. For example, scanning control routine 122 may control the transitioning from measurements in the low magnification optical mode for a rapidly changing topography (e.g., 2 to 3 microns) to measurements in the high magnification AFM and/or STM mode for a region (e.g., n on a side) which might be expected to be locally planar, atomic, and/or conductive.

Display Control

Figure 10A:
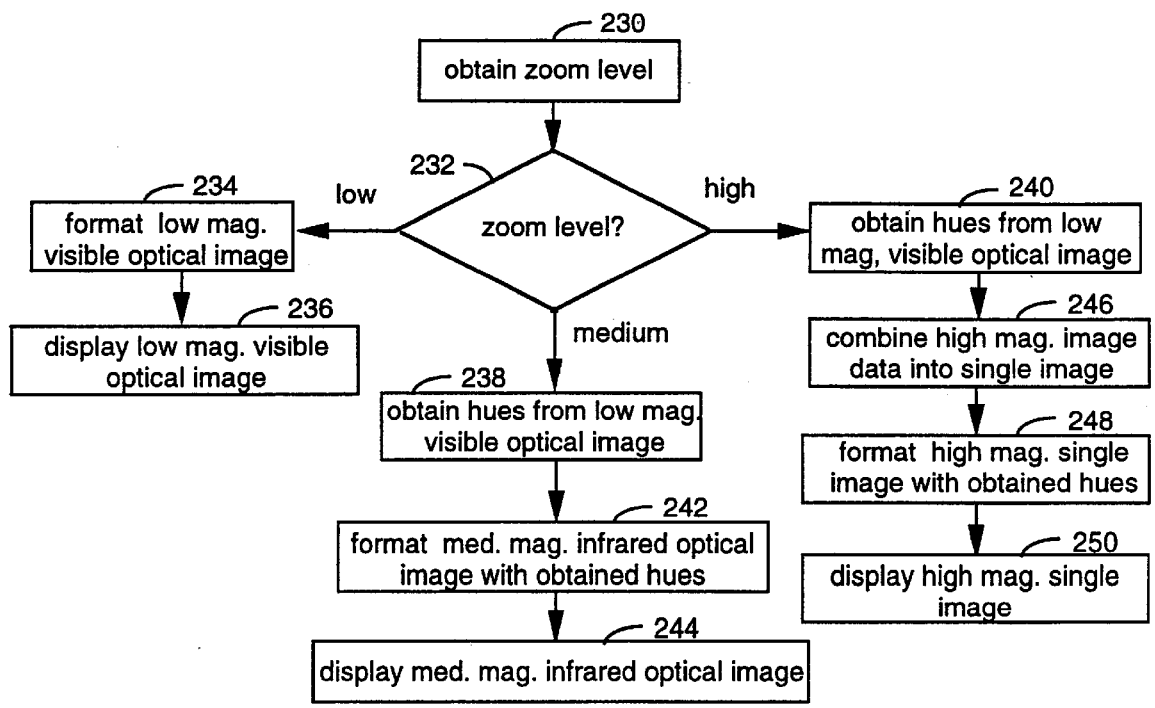
FIGS. 10a and 10b show the display sequence of the scanning probe microscope assembly of FIG. 1.

FIG. 10a shows the display control sequence controlled by the display routine 136 in the case where the medium magnification optical microscopy mode is based on infrared light measurements in the way described earlier.

The display routine 136 first obtains the zoom (i.e., magnification) level desired by the user (block 230). The user requests the zoom level with control terminal 116 which issues a zoom level command signal containing data representing the desired zoom level. This signal is received by the CPU 120 and the display routine 136 in response obtains the desired zoom level.

The display routine 136 then determines the desired zoom level from the data contained in the received zoom level command signal (block 232).

If the desired zoom level is a low magnification zoom level, then display routine 136 formats the visible optical image data provided by the visible optical microscopy analysis routine 139 (block 234). This formatted data is then provided to the display monitor for display of the represented image (block 236).

If the desired zoom level is a medium or high magnification zoom level, then display routine 136 first obtains the hues of the low magnification visible optical image data provided by the visible optical microscopy analysis routine 139 (blocks 238 and 240).

In the case of a medium magnification zoom level, display routine 136 uses the visible optical image hues to format the infrared optical image data provided by the optical microscopy analysis routine 141 so that it has a color pattern consistent with the visible optical image (block 242). The formatted data is then provided to the display monitor 118 for display of the represented image (block 244).

In the case of a high magnification zoom level, as was suggested earlier, display routine 136 overlays and combines the recorded image data representing the various measurements made during the high magnification scan into a single high magnification image of the object 104 using conventional data processing techniques (block 246). In this way, the data produced by the AFM or STM analysis routines 137 or 138 representing the primary high magnification measurements provides the basic image data. This basic image data is augmented with data produced by the near-field optical analysis routine 151 providing image data on deep surface features. It is also augmented with data produced by the STM or AFM analysis routines 138 or 137 representing the secondary high magnification measurements and providing image data on local variations in the composition or conductivity of object 104. Moreover, the basic image data is augmented with data produced by the spectrophotometric and hardness testing analysis routines 143, 149, and 195 providing further image data on local variations of the composition of object 104.

After the single high magnification image is produced by the display routine 136, it uses the visible optical image hues to format the single image so that it has a color pattern consistent with the visible optical image (block 248). Where the visible optical image color differences are smaller than the infrared optical image gray scale differences, intermediate hues are created by display routine 136 around the visible optical image hues using the visible optical image hues as the center for variation. The formatted data is then provided to the display monitor for display of the represented image (block 250).

Figure 10B:
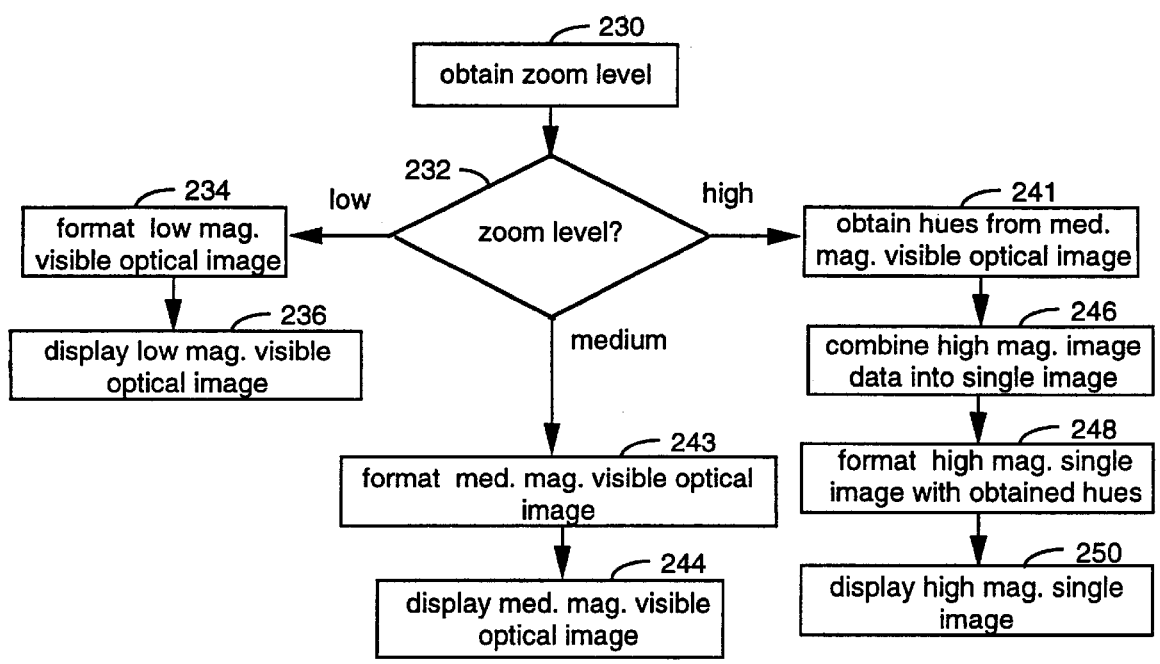

FIG. 10b shows the display control sequence controlled by the display routine 136 in the case where the medium magnification optical microscopy mode is based on visible light measurements, as discussed earlier. Here, the hues of the low magnification visible optical image need not be obtained for formatting the medium magnification visible optical image since this image necessarily would have the same hues (block 243). Moreover, the hues for formatting the high magnification image would be obtained from the medium magnification visible optical image (block 241) since the color differences may be more pronounced thereby providing more hue information.

Since scanning probe microscope assembly 100 is configured to produce high, medium, and low magnification images with a consistent color pattern, the user is provided with continuous single image zoom.

DESCRIPTION OF THE SECOND EMBODIMENT

Figure 11:
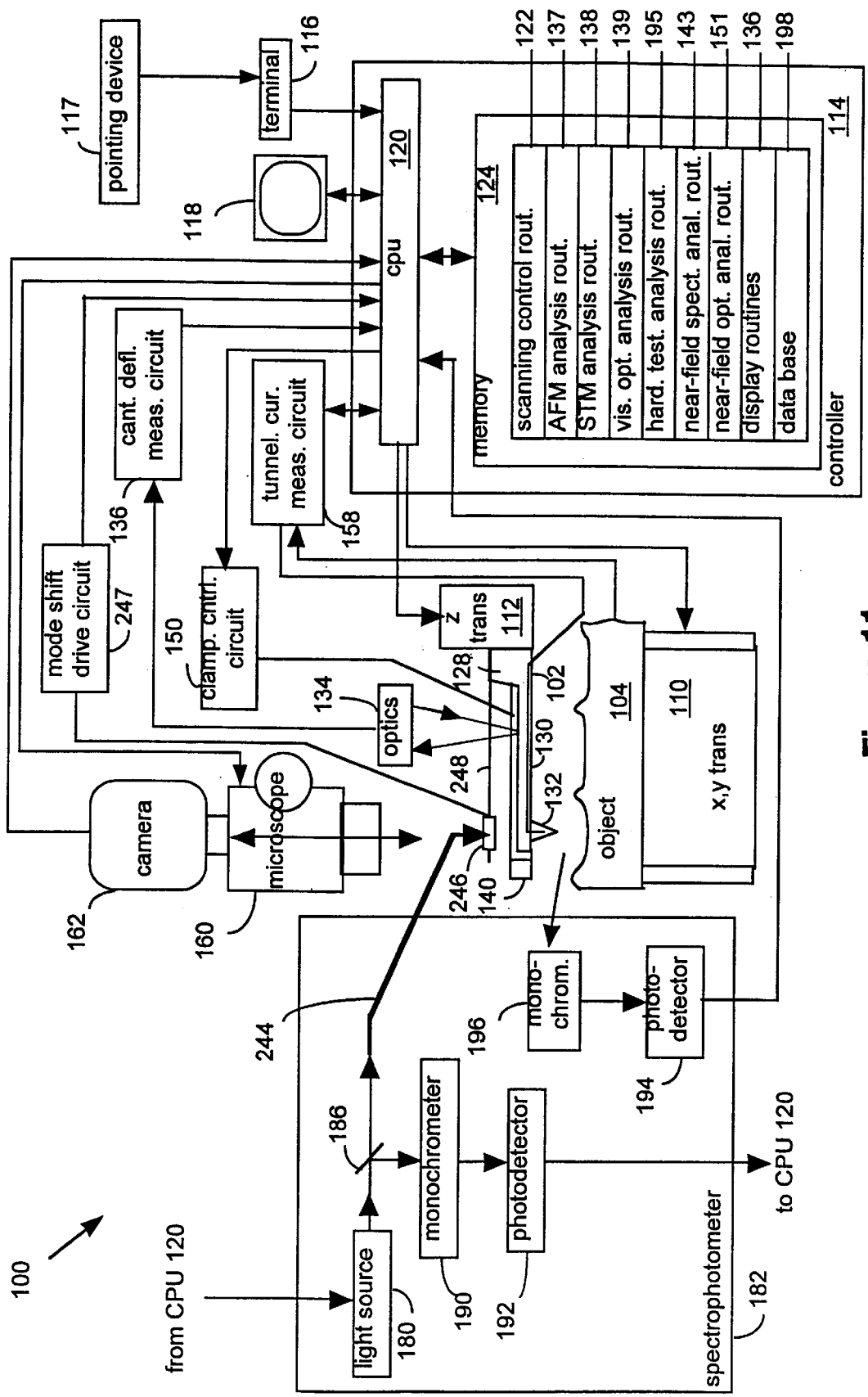
FIG. 11 shows another conceptual view of a scanning probe microscope assembly in accordance with the present invention.

Referring to FIG. 11, there is shown a conceptual diagram of another embodiment of a scanning probe microscope assembly 100 in accordance with the present invention. In this embodiment, scanning probe microscope assembly 100 includes a fiber optic light guide 244 for guiding the light 185 provided by the light source 180 to the probe 102.

Figure 12A:
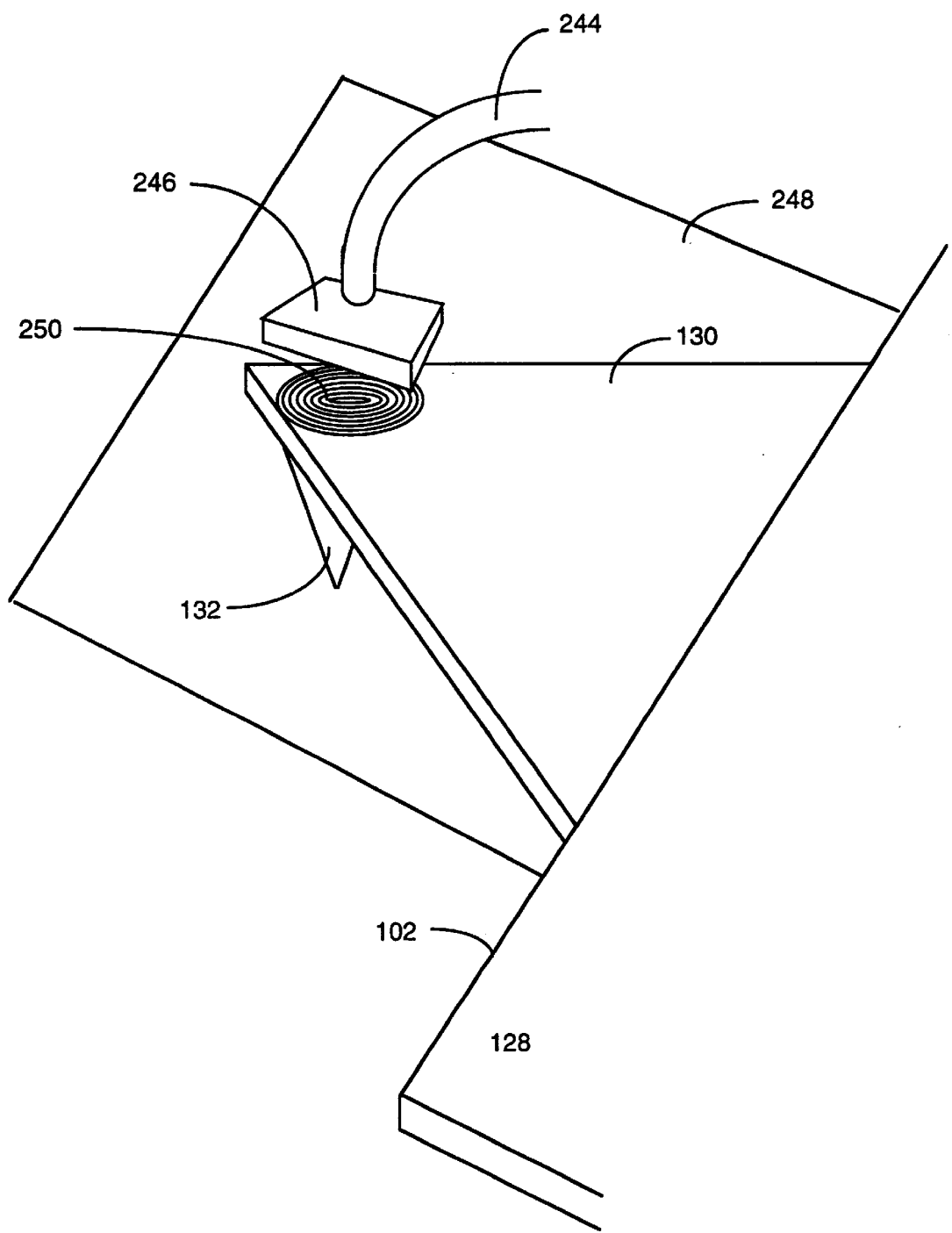
FIGS. 12a shows the probe of the scanning probe microscope assembly of FIG. 11 with a mode shifter and a fresnel lens over the tip of the probe.
Figure 12B:
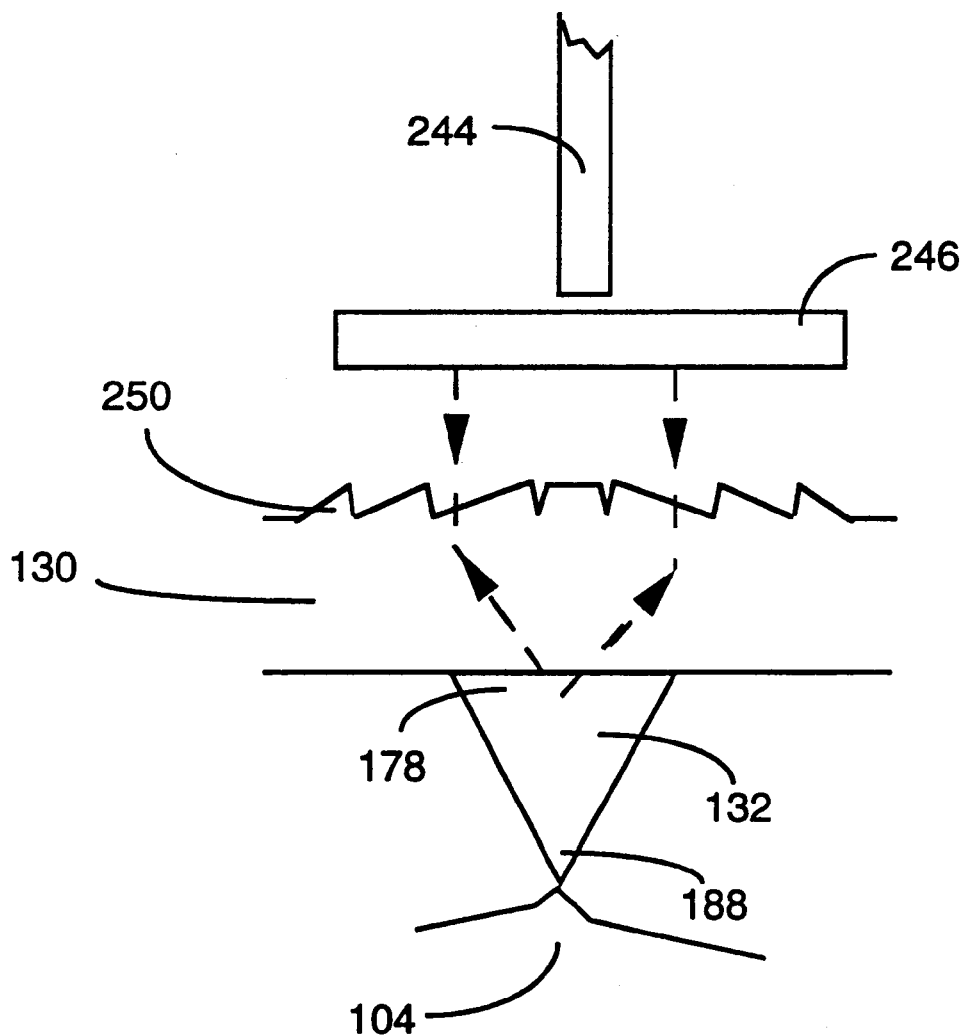

As shown in FIGS. 12a and 12b, the light guide 244 is optically coupled to an electro-optic mode shifter 246. Referring to FIG. 12a, the mode shifter 246 is held and supported by a thin support 248 connected to the base 128 of the probe 102 and is disposed over the fine fresnel lens 250 formed in the cantilever 130. The support 248 is transparent to visible light.

The electro-optic mode shifter 246 may be a plane polarizer on top of a liquid crystal in conjunction with a wave plate and is connected to the light guide 244 with optical cement. The plane polarizer of the mode shifter 246 plane polarizes the light received from the light guide 244. At the same time, the scanning control routine 122 generates control signals for controlling the mode shift drive circuit 247 to apply a variable voltage to the liquid crystal. In response to the applied voltage, the liquid crystal rotates the plane polarized light and the wave plate in response alternatingly produces right circular, elliptical, and left circular polarized light provided to the frensel lens 250. In other words, the mode shifter 246 continuously changes the polarization state of the light provided by the light source 180 during the near-field optical mode.

Alternatively, a mechanically rotatable plane polarizer such as polarizer 184 of FIG. 1 may be used to rotationally polarize the light provided by the light source 180. In this configuration, the mode shifter 246 includes only the wave plate. When scanning control routine 122 generates control signals for controlling the polarizer 184 to rotationally plane polarize the light provided to the mode shifter 246, then right circular, elliptical, and left circular light is alternatingly produced during the near-field optical mode by the wave plate of the mode shifter 246.

However, those skilled in the art will appreciate that other configurations may be employed for rotating or continuously changing the polar state of the light 185 during the near-field optical mode. For example, the mode shifter 246 may be entirely omitted with the light 185 being rotationally polarized as was described for the configuration of FIG. 1. Also, the mode shifter 246 may include a ferro-optic liquid crystal (with the wave plate being omitted) that may be electrically excited to change the polarization state. Or, the mode shifter may be a Pockels cell (with the wave plate being omitted) that may be excited with an electric field to change the polarization state. Moreover, a mechanically rotatable Glan prism may be used.

Referring to FIG. 12b, the light 185 provided by the light guide 244 to the mode shifter 246 is passed to the fresnel lens 250 and then focussed within the base 178 of the tip 132 by the fresnel lens 250. As was indicated earlier, the light 185 focused within the base 178 propagates through the tip 132 and is emitted at the sharp end 188 of the tip 132. The emitted light 185 optically interacts with the object 104 and the sharp end 188 of the tip 132 captures the resulting light due to the optical interaction of the emitted light with the object 104. This light propagates back through the tip 132 to the fresnel lens 250 which provides it to the mode shifter 246. From there, it is provided to the light guide 244 which guides the light back to the spectrophotometer 180 for spectrophotometric measurements in the same way as was described earlier. Moreover, photoemissive energy due to the optical interaction is detected by the photodetector 194 as was the case in the embodiment of FIG. 1.

This embodiment includes all of the modalities described above for the embodiment of FIG. 1 except the medium magnification mode.

DESCRIPTION OF THIRD EMBODIMENT

Figure 13:
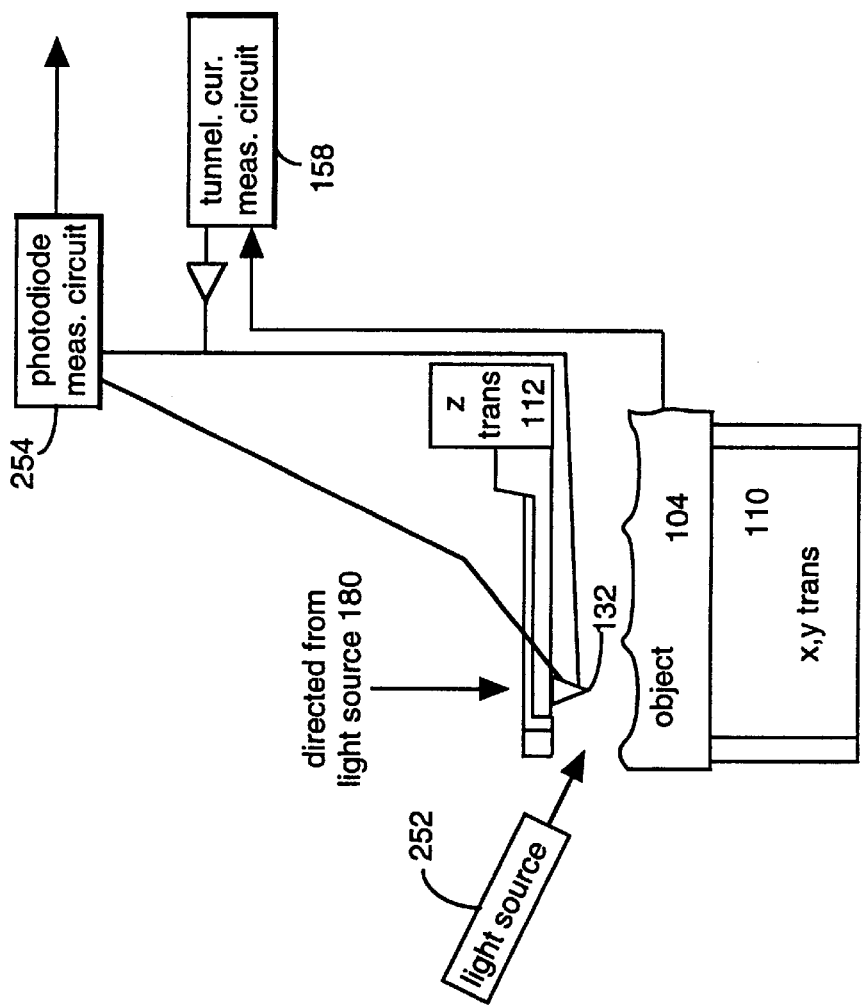
FIG. 13 shows still another conceptual view of a scanning probe microscope assembly in accordance with the present invention.
Figure 14:
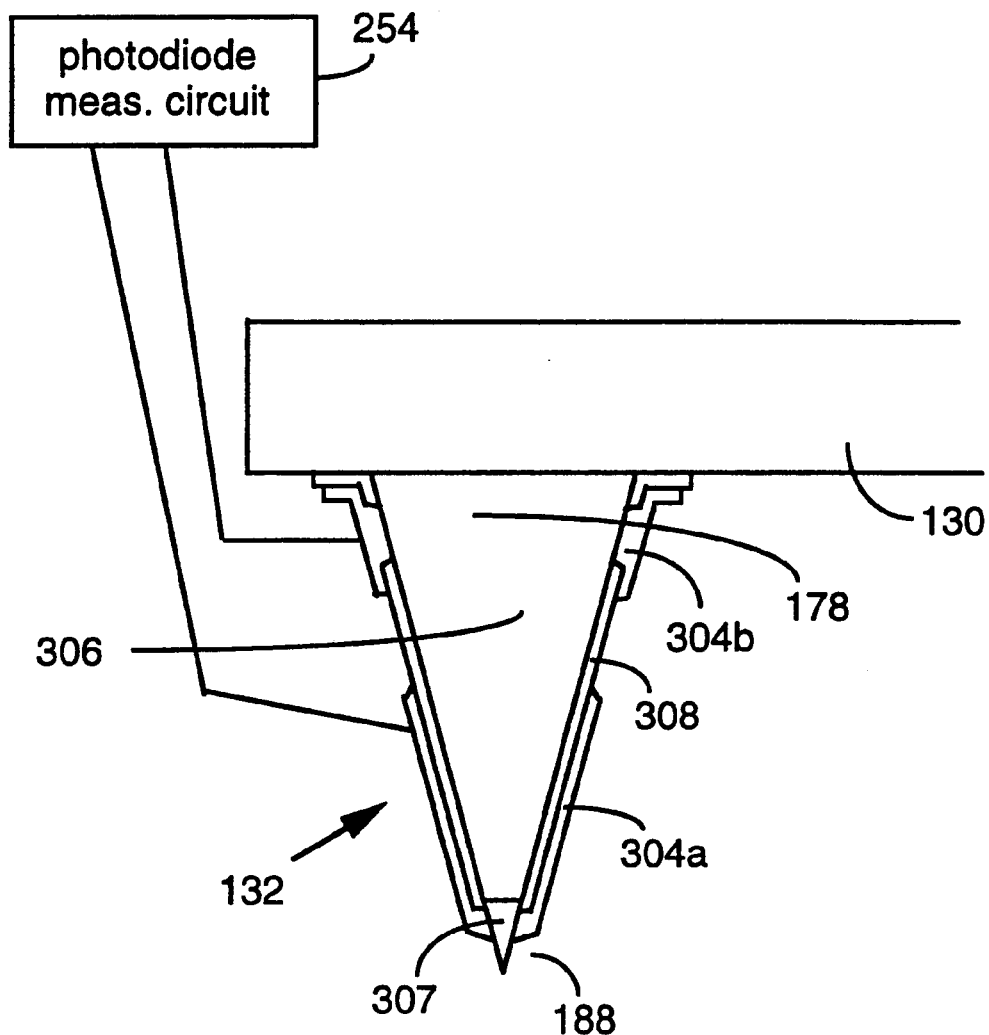
FIG. 14 shows the photodiode tip of the probe of the scanning probe microscope assembly of FIG. 13.

FIG. 13 in conjunction with FIG. 14 provides a variation to the embodiments of FIGS. 1 and 11. In this embodiment, a photodiode is built into the tip 132 for making near-field spectrophotometric measurements similar to those described earlier.

Referring to FIG. 14, the bulk silicon portion 306 of the tip 132 is doped to be N or P type and then oxidized so as to have a thick silicon dioxide layer 308. A small region 307 (e.g., approximately 10 nm) at the sharp end 188 of the silicon tip 132 is oppositely doped (P or N doped) to the bulk silicon portion 306 and oxidation etched.

Then, the entire tip 132 is lightly overcoated with a conductive material such as doped silicon carbide, aluminum, tungsten, gold, or other appropriate conductor and then etched to form the conductive contacts 304a and 304b. Similar to the tips 132 of FIGS. 8a–8d, the conductive coating 304a is removed or rubbed off from the sharp end 188 of the tip 132. Or, if the conductive coating 304a is a sufficiently light metal layer, it may pass an adequate amount of light without being removed. Moreover, if the conductive coating 304a is a conductive optically transparent material like doped silicon carbide, then it need not be removed at all.

In any case, this is all done through conventional techniques known to those skilled in the art and results in a tip 132 with a PN or NP junction confined to a very small region of the tip 132 at the sharp end 188. This small Junction area forms the effective aperture of the tip 132.

Referring to FIG. 13, in operation, an external light source 252 may be used to illuminate the region of the tip at the object 104 for spectrophotometric measurements made with the photodiode. Alternatively, infrared light 185 may be provided to the tip 132 in the ways described for FIGS. 1 an 11. The light 185 is emitted by tip 132 to induce Raman, second harmonic radiation, florescence or other photoemissive modes at the surface of the object 104 beneath the tip 132. In either case, the optical energy detected by the photodiode is represented by a voltage across the metal contacts 304a and 304b of FIG. 14 and is provided to the photodiode measurement circuit 254 which measures the optical energy and provides the CPU 120 with a signal containing data representing the measured optical energy. This data is then analyzed and processed by the near-field spectrophotometry analysis routine 143 in the same way as was discussed earlier for the data received from the photodetector 192.

DESCRIPTION OF FOURTH EMBODIMENT

Figure 15:
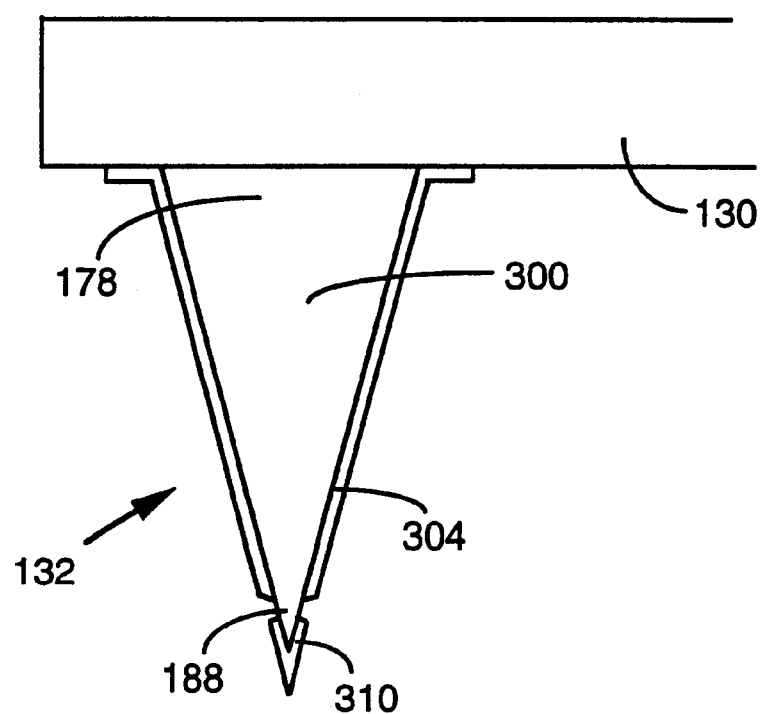
FIG. 15 shows a tip of a probe for use with the scanning probe micrscope assembly of FIGS. 1 and 11.

FIG. 15 shows another variation of tip 132 for the embodiments of FIGS. 1 and 11. In this case, a coating 310 of an material emissive material, such as gallium nitride or gallium arsenide, or a non-linear frequency doubling material, such as potassium niobate or lithium titanate, is coated over a small region of the core material 300 at the sharp end 188 of the tip 132. The coating 310 extends approximately a few Angstroms to 10's of Angstroms from the point of the sharp end 188 and has a thickness in the range of approximately 0.5 to 500 Angstroms.

The conductive coating 304 over the core material 300 of the tip 132 ends approximately few 10's of nm away from the point of the sharp end 188 of tip 132. Thus, the spatial resolution in the near-field of this arrangement is limited only by the size of this material rather then the electromagnetic confinement properties of the coatings on tip 132 or the smoothness of tip 132. In other words, the aperture of tip 132 at the sharp end 188 is formed by the coating 310.

Light 185 may be provided to the tip 132 in the ways described for FIGS. 1 and 11. This light propagates down the tip 132 and interacts with the coating 310 and is emitted at the sharp end 188. This light may induce Raman, second harmonic radiation, florescence or other photoemissive modes at the surface of the object 104 beneath the tip 132 for the near-field spectrophotometric mode or may be used in the way described earlier for the near-field optical mode. The light resulting from the optical interaction with the object 104 is detected by photodetector 194.

DESCRIPTION OF THE FIFTH EMBODIMENT

Figure 16:
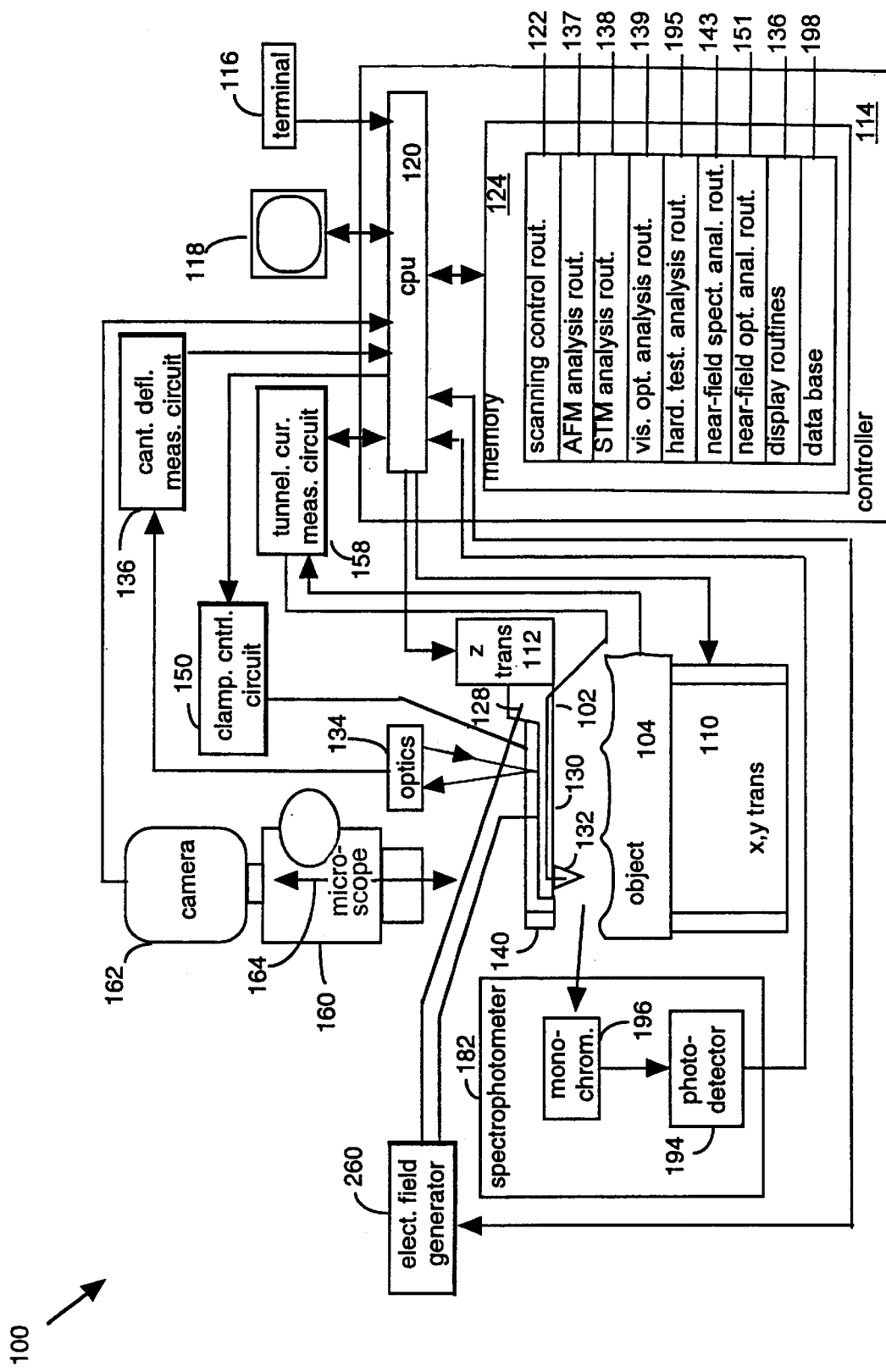
FIG. 16 shows yet another conceptual view of a scanning probe microscope assembly in accordance with the present invention.

Referring to FIG. 16, there is shown a conceptual diagram of still another embodiment of a scanning probe microscope assembly 100 in accordance with the present invention. In this embodiment, scanning probe microscope assembly 100 includes an electric field generator 260 for applying an electric field to the probe 102 so that light including blue and/or ultraviolet light is emitted by the tip 132 in response.

Figure 17A:
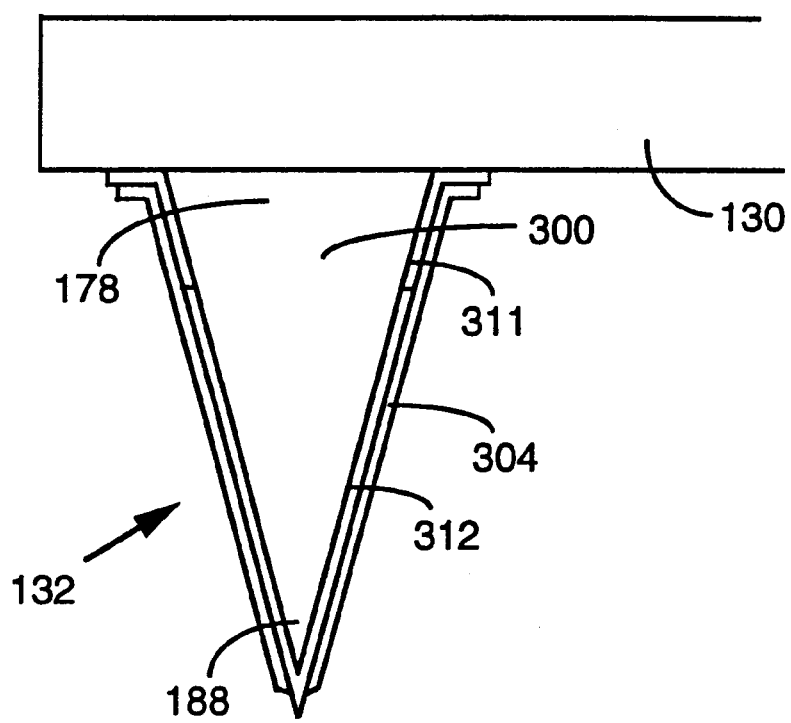
FIGS. 17a–17c show light emissive tips for use with the scanning probe microscope assembly of FIG. 16.

As shown in FIG. 17a, the core material 300 of the tip 132 at the base 178 and the core material 300 of the cantilever 130 around the base 178 are first coated with an emissive material 311 such as gallium nitride or gallium arsenide at a thickness of approximately 10 to 200 nm. Then, the tip 132 is coated with an insulating material 312 such as diamond, silicon carbide, carbon nitride, or silicon dioxide with a thickness of approximately 1 to 10 nm. The portion of the coating 312 over the emissive material 311 is removed using conventional techniques and then a conductive layer 304 of aluminum, gold, tungsten, or some other conductor is formed over the emissive material 311 and the coating 312 with a thickness of approximately 20 to 200 nm. Similar to the tips 132 of FIGS. 8a–8d, the conductive coating 304 is removed or rubbed off from the sharp end 188 of the tip 132 to form an aperture near the sharp end 188.

Referring back to FIG. 16, during the near-field spectrophotometry mode describe earlier, scanning control routine 122 controls the electric field generator 260 to generate an electrical field (voltage). This is applied between the outside conductive layer 304 shown in FIG. 17a and the core silicon material 300 of the probe 102. As a result, with an applied voltage of approximately 4 volts, blue (423 nm) and ultraviolet light (372 nm) is emitted by the emissive coating 310 as described in *and Fabrication in Monocrystalline Alpha and Beta Silicon Carbide*, by Robert F. Davis, Journal of Vacuum Science and Technology, volume A 11(41) (July/August 1993). The light propagates through the tip 132 until it is emitted at the sharp end 188 of the tip 132 in a small region substantially smaller than the wavelength of the light.

Figure 17B:
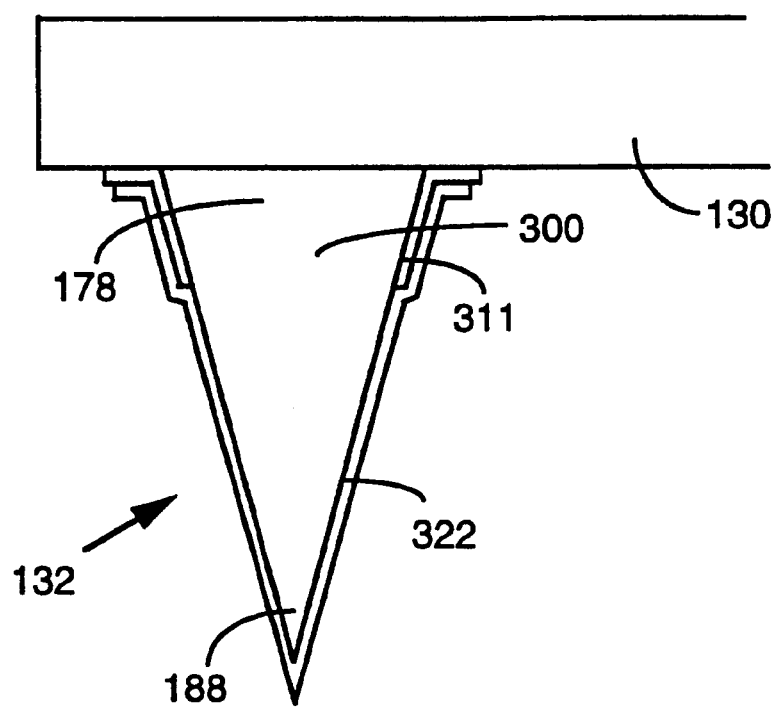

Alternatively, as shown in FIG. 17b, a silicon carbide coating 322 over the emissive coating 311 may be doped to be conductive. As a result, the conductive coating 304 would be omitted and a voltage would be applied by the electric field generator 260 across the core silicon material 300 and the silicon carbide coating 312 so that the emissive coating 311 produces the blue and ultraviolet light.

Figure 17C:
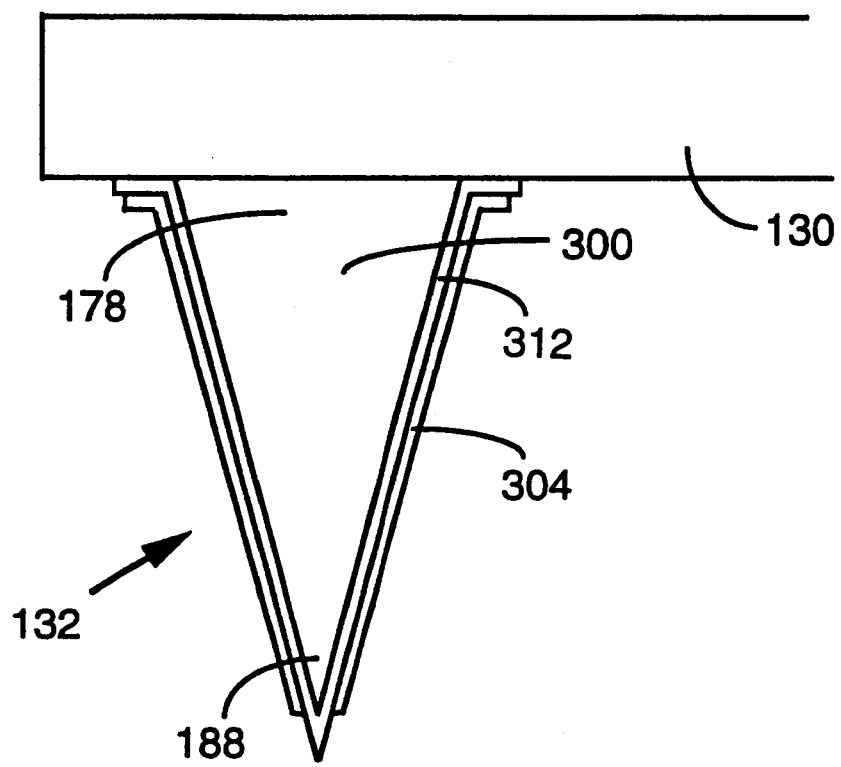

Moreover, as shown in FIG. 17c, the core silicon material 300 of the cantilever 130 and tip 132 may be first coated with a silicon carbide layer 312. The silicon carbide is then doped to be emissive in the way described in *Deposition and Fabrication in Monocrystalline Alpha and Beta Silicon Carbide*. Then, a conductive layer 304 of aluminum, gold, tungsten, or some other conductor is formed over the silicon carbide layer 312. Similar to the tips 132 of FIGS. 8a–8d, the conductive coating 304 is removed or rubbed off from the sharp end 188 of the tip 132 to form an aperture near the sharp end 188. An applied voltage between the conductive layer 304 and the core silicon material 300 results in blue light being emitted by the silicon carbide layer 322, as described in *Deposition and Fabrication in Monocrystalline Alpha and Beta Silicon Carbide*. The light energy propagates through the tip 132 until it is emitted at the sharp end 188 of the tip 132.

In each of the configurations described above, photoemissive energy due to the optical interaction is detected by the photodetector 194 in the near-field spectrophotometry and optical modes in the same way as described for the embodiment of FIG. 1.

DESCRIPTION OF THE SIXTH EMBODIMENT

Figure 18:
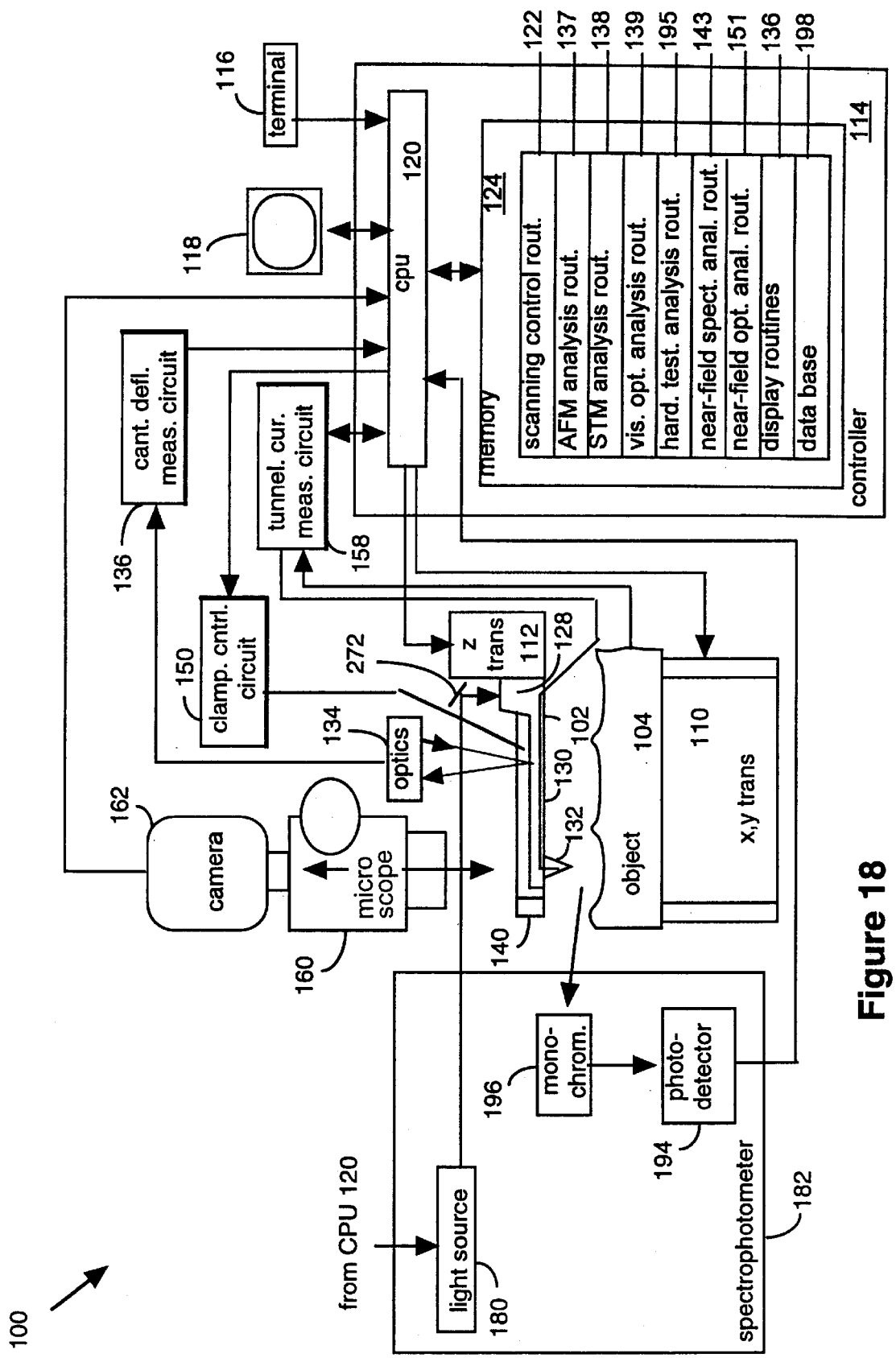
FIG. 18 shows one more conceptual view of a scanning probe microscope assembly in accordance with the present invention.

Referring to FIG. 18, there is shown a conceptual diagram of yet another embodiment of a scanning probe microscope assembly 100 in accordance with the present invention. In this embodiment, scanning probe microscope assembly 100 includes an infrared light source 270 and mirror 272 for providing infrared light 273 to the base 128 of the probe 102. Alternatively, a fiber optic light guide such as the one shown in FIG. 11 may be used to provide the light 273 to the base 128 of the probe 102.

Figure 19A:
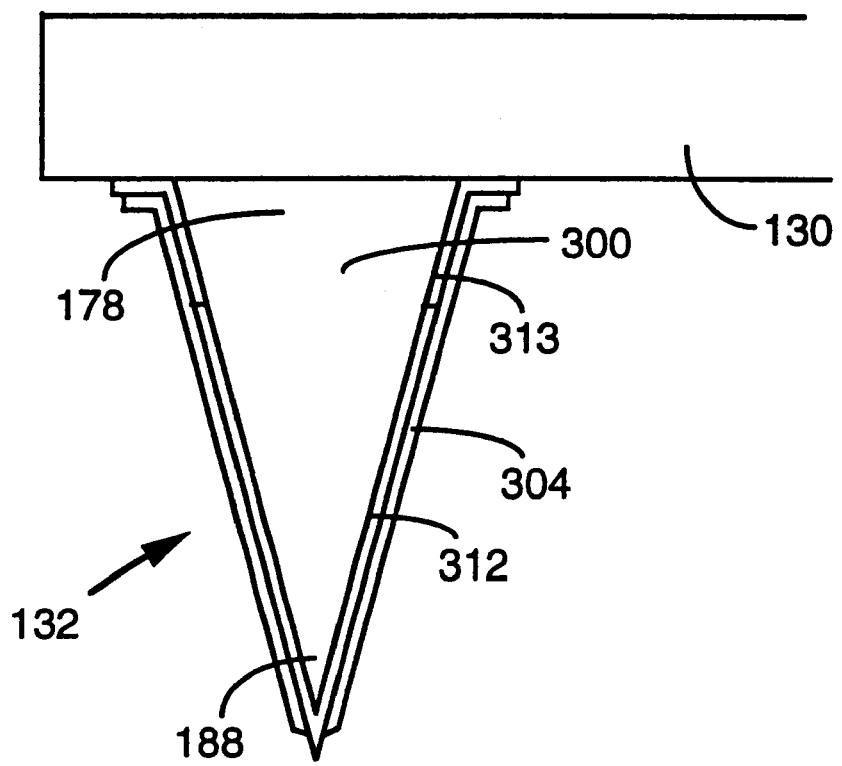
FIG. 19a shows a frequency doubling tip and cantilever for use with the scanning probe microscope assembly of FIG. 18.

As shown in FIG. 19a, the core material 300 of the cantilever 130 near the base 178 of the tip 132 is first coated with a non-linear frequency doubling emissive material 313 such as potassium niobate or lithium titanate. Then, the tip 132 is coated with an obdurate material or insulator 312 such as diamond, silicon carbide, or silicon dioxide. The portion of the coating 312 over the frequency doubling material 313 is removed using conventional techniques and then a conductive layer 304 of aluminum, gold, tungsten, or some other conductor is formed over the frequency doubling emissive material 313 and the coating 312. Similar to the tips 132 of FIGS. 8a–8d, the conductive coating 304 is removed or rubbed off from the sharp end 188 of the tip 132 to form an aperture near the sharp end 188.

Figure 19B:
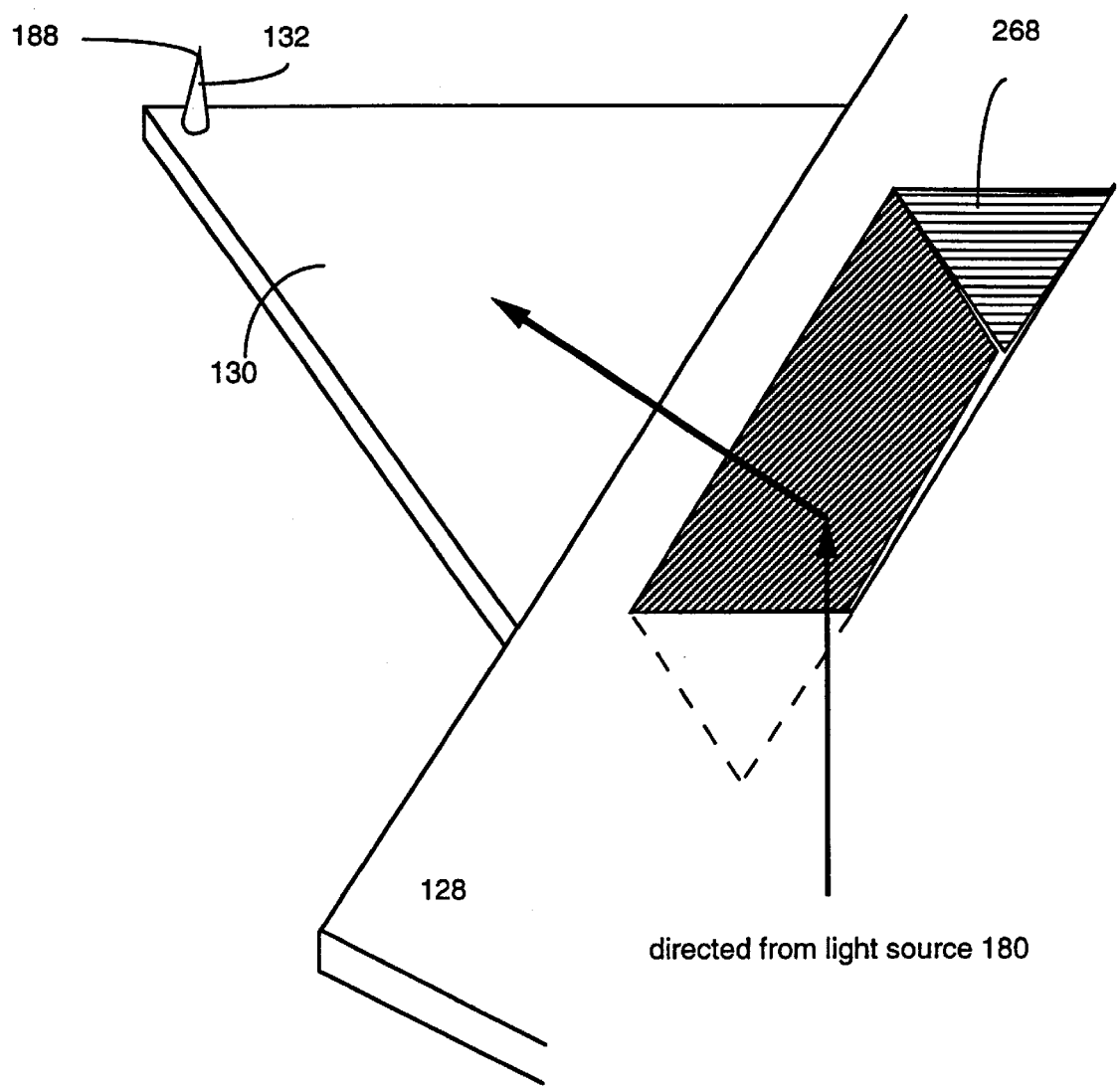
FIG. 19b shows trench reflector for use with the scanning probe microscope assembly of FIG. 18.

As shown in FIG. 19b, an elongated pyramid shaped trench (or similar reflecting structure) 268 is etched into the bottom of the base 128 to form a reflecting surface. This trench 268 directs the infrared light 273 into the cantilever 130 where it will be frequency doubled by the frequency doubling material 330. The frequency doubled light energy propagates through the tip 132 until it is emitted at the sharp end 188 of the tip 132.

In this embodiment, photoemissive energy due to the optical interaction is detected by the photodetector 194 in the same way as described or the embodiment of FIG. 1. And, the near-field spectrophotometry and optical modes are not included in this embodiment but the other modalities described above for the embodiment of FIG. 1 are still included.

While the present invention has been described with reference to a few specific embodiments, the description is illustrative of the invention and is not to be construed as limiting the invention. Furthermore, various other modifications may occur to those skilled in the art without departing from the true spirit and scope of the invention as defined by the appended claims.

What is claimed is:

1. A scanning probe microscope assembly for examining an object, comprising:
    a probe comprising a tip, said tip having a sharp end and a base;
    at least one light source optically coupled to said tip for providing a narrow beam of light and a wide beam of light;
    a lens system disposed over said base of said tip and optically coupled between said light source and said tip, said lens system focusing said provided narrow beam of light in said base of said tip so that said focused narrow beam of light propagates in said tip, said lens system focusing said provided wide beam of light on said object so that said object reflects said focused wide beam of light back to said lens;
    wide beam receiving means optically coupled to said lens system for receiving said reflected wide beam of light;
    said tip being formed so as to emit said propagating narrow beam of light at said sharp end so that said emitted narrow beam of light optically interacts with said object; and
    a photodetector for detecting light resulting from said emitted narrow beam of light optically interacting with said object.

2. A scanning probe microscope assembly as recited in claim 1 further comprising;
    a monochrometer for separating said resulting light into its constituent wavelengths;
    said photodetector optically coupled to said monochrometer for detecting said wavelengths.

3. A scanning probe microscope assembly as recited in claim 1 wherein said lens system comprises a refractive lens.

4. A scanning probe microscope assembly as recited in claim 1 wherein:
    said tip is further formed so as to capture said resulting light so that said captured light propagates in said tip to said lens system;
    said photodetector is optically coupled to said lens system for detecting said captured light.

5. A scanning probe microscope assembly as recited in claim 1 further comprising non-optical interaction means for inducing and detecting non-optical interaction between said tip and said object.

6. A scanning probe microscope assembly as recited in claim 5 wherein:
    said probe includes a cantilever to which said tip is connected; and
    said non-optical interaction means includes atomic force means for inducing atomic force interaction between said tip and said object and for detecting deflection of said cantilever due to said atomic force interaction.

7. A scanning probe microscope assembly as recited in claim 5 wherein said non-optical interaction means includes tunneling current means for inducing and detecting a tunneling current between said tip and said object.

8. A scanning probe microscope assembly as recited in claim 5 wherein said scanning probe microscope assembly includes low, medium, and high magnification modes and further comprises:
    visible light illuminating and detection means for illuminating said object with visible light so that said visible light is reflected by said object and for detecting said reflected visible light;
    scanning control means for controlling said scanning probe microscope assembly to perform (1) when said low magnification mode is selected, a low magnification scan with said visible light illuminating and detection means, (2) when said medium magnification mode is selected, a medium magnification scan with said at least one light source and said wide beam detection means, and (3) when said high magnification mode is selected, a high magnification scan with said at least one light source, said photodetector, and said non-optical interaction means;

low magnification mode analysis means for making during said low magnification scan low magnification measurements of said detected visible light and generating in response low magnification image data of said object;

medium magnification mode analysis means for making during said medium magnification scan medium magnification measurements of said detected wide beam of light and generating in response medium magnification image data of said object;

high magnification mode analysis means for making during said high magnification scan high magnification measurements of said detected non-optical interaction and said detected resulting light and generating in response high magnification image data of said object; and display means for displaying (1) when said low magnification mode is selected, a low magnification image of said object from said low magnification image data, (2) when said medium magnification mode is selected, a medium magnification image of said object from said medium magnification image data, and (3) when said high magnification mode is selected, a high magnification image of said object from said high magnification image data.

9. A scanning probe microscope assembly for examining an object, comprising:

a light source to provide light that optically interacts with said object;

a probe comprising a tip having:
a sharp end:
an aperture at said sharp end of said tip to capture light resulting from said provided light optically interacting with said object; and
a photodiode formed in said tip for detecting said captured light.

10. A scanning probe microscope assembly as recited in claim 9 wherein:
said photodiode comprises:
a first doped silicon region in said tip;
a second doped silicon region in said tip oppositely doped to and in contact with said first doped silicon region;
a first conductive coating in contact with said first doped silicon region;
a second conductive coating in contact with said second doped silicon region;
a photodiode measurement circuit coupled across said first and second conductive coatings for making measurements of said detected light.

11. A scanning probe microscope assembly as recited in claim 10 wherein:
said first doped silicon region is at said sharp end of said tip and said second doped silicon region is above said first doped silicon region;
said first conductive coating is transparent at or not over said sharp end of said tip to form said aperture.

12. A scanning probe microscope assembly as recited in claim 9 wherein said light source illuminates said object with said provided light.

13. A scanning probe microscope assembly as recited in claim 9 wherein:
said light source is optically coupled to said tip to direct said provided light to said tip;
said tip is formed so that said provided light propagates through said tip, is emitted by said aperture, and optically interacts with said object to produce said resulting light.

14. A scanning probe microscope assembly as recited in claim 10 further comprising non-optical interaction means for inducing and detecting non-optical interaction of said tip and said object.

15. A scanning probe microscope assembly as recited in claim 14 wherein said non-optical interaction means comprises tunneling current means for inducing and detecting a tunneling current between said tip and said object using said first conductive coating.

16. A scanning probe microscope assembly as recited in claim 14 wherein:
said probe includes a cantilever to which said tip is connected;
said non-optical interaction means comprises atomic force means for inducing atomic force interaction between said tip and said object and for detecting deflection of said cantilever due to said atomic force interaction.

17. A scanning probe microscope assembly for examining an object, comprising:
a probe comprising a tip having:
a sharp end;
a core material extending to the sharp end;
a light emissive layer over at least a portion of said core material; and
a conductive layer over said light emissive layer;
an aperture at the sharp end formed by said emissive layer not being over said core material at said sharp end and said conductive layer being transparent at or not over said core material at said sharp end to form said aperture;
means for applying a voltage between said conductive layer and said core material so that said light emissive layer emits light that propagates through said core material and is emitted at said aperture, said emitted light optically interacting with said object; and
a photodetector for detecting light resulting from said emitted light optically interacting with said object.

18. A scanning probe microscope assembly as recited in claim 17 wherein said light emissive layer comprises gallium nitride.

19. A scanning probe microscope assembly as recited in claim 17 wherein said light emissive layer comprises gallium arsenide.

20. A scanning probe microscope assembly as recited in claim 17 wherein said light emissive layer comprises silicon carbide doped to be emissive.

21. A scanning probe microscope assembly as recited in claim 17 further comprising means for inducing and detecting non-optical interaction of said tip and said object.

22. A scanning probe microscope assembly as recited in claim 21 wherein:
said probe further includes a cantilever connected to said tip; and
said non-optical interaction means comprises atomic force means for inducing atomic force interaction between said tip and said object and for detecting deflection of said cantilever due to said atomic force interaction.

23. A scanning probe microscope assembly as recited in claim 21 wherein:
said non-optical interaction means comprises tunneling current means for inducing and detecting a tunneling current between said tip and said object;
said conductive layer is formed for use in inducing and detecting said non-optical interaction of said tip and said object.

24. A scanning probe microscope assembly for examining an object, said scanning probe microscope assembly having a scanning tunneling microscopy mode and an atomic force microscopy mode, said scanning probe microscope assembly comprising:
a probe having a base, a cantilever connected to said base, and a tip connected to said cantilever;
tunneling current means for inducing and detecting a tunneling current between said tip and said object during said scanning tunneling microscopy mode; and
atomic force means for inducing atomic force interaction between said tip and said object and for detecting deflection of said cantilever due to said atomic force interaction during said atomic force microscopy mode;
holding means for holding said cantilever rigid with respect to said base during said scanning tunneling microscopy mode.

25. A scanning probe microscope assembly as recited in claim 24 wherein said holding means includes:
a clamping structure connected to said base; and
clamping control means for controlling said clamping structure to hold said cantilever rigid with respect to said base during said scanning tunneling microscopy mode.

26. A scanning probe microscope assembly as recited in claim 25 wherein:
said cantilever has a free end adjacent to said tip;
said clamping structure comprises a clamping arm extending from said base and having a free end extending past and opposing said free end of said cantilever; and
said clamping control means controls movement of said free end of said clamping arm against said free end of said cantilever during said scanning tunneling microscopy mode to hold said cantilever rigid with respect to said base.

27. A scanning probe microscope assembly as recited in claim 25 wherein:
said clamping structure surrounds said cantilever and includes clamping arms; and
said clamping control means controls movement of said clamping arms against said cantilever during said scanning tunneling microscopy mode to hold said cantilever rigid with respect to said base.

28. A scanning probe microscope assembly as recited in claim 24 wherein:
said cantilever has a lower surface to which said tip is connected and an upper surface;
said holding means includes:
a member coupled to said base and having a lower surface disposed over said upper surface of said cantilever;
an insulating layer on one of said upper surface of said cantilever and said lower surface of said member;
means for applying a voltage between said member and said cantilever to electrostatically hold said cantilever rigid with respect to said base during said scanning tunneling microscopy mode.

29. A scanning probe microscope assembly as recited in claim 24 wherein:
said cantilever has a lower surface to which said tip is connected and an upper surface;
said holding means includes:
a member coupled to said base and having a lower surface disposed over said upper surface of said cantilever;
a first coil on said upper surface of said cantilever;
a second coil on said lower surface of said member;
means for producing currents in said coils to magnetically hold said cantilever rigid with respect to said base during said scanning tunneling microscopy mode.

30. A scanning probe microscope assembly as recited in claim 24 wherein:
said cantilever has a lower surface to which said tip is connected and an upper surface;
said holding means includes:
a member coupled to said base and having a lower surface disposed over said upper surface of said cantilever;
a permanent magnet and a coil on different ones of said upper surface of said cantilever and said lower surface of said member; and
means for producing a current in said coil to magnetically hold said cantilever rigid with respect to said base during said scanning tunneling microscopy mode.

31. A scanning probe microscope assembly as recited in claim 24 wherein said scanning probe microscope assembly also has additional mode and further comprises:
a light source optically coupled to said tip; to provide light to said tip during said additional mode so that said provided light propagates in said tip;
said tip being formed so as to emit said provided light at said sharp end so that said emitted light optically interacts with said object;
a photodetector for detecting light that results from said emitted light optically interacting with said object.

32. A scanning probe microscopy probe comprising a tip having:
a sharp end;
a core material extending to said sharp end;
a light emissive layer over said core material; and
a conductive layer over said light emissive layer;
an aperture at the sharp end formed by said emissive layer not being over said core material at said sharp end and said conductive layer being transparent at or not over said core material at said sharp end to form said aperture;
said emissive layer producing light when a voltage is applied across said conductive layer and said core material, said produced light propagating through said core material and being emitted at said aperture.

33. A probe as recited in claim 32 wherein said light emissive layer comprises gallium nitride.

34. A probe as recited in claim 32 wherein said light emissive layer comprises gallium arsenide.

35. A probe as recited in claim 32 wherein said light emissive layer comprises silicon carbide doped to be light emissive.

36. A probe as recited in claim 32 further comprising a centelever connected to said tip for use in inducing atomic force interaction of said tip and said object and for detecting deflection of said cantilever due to said atomic force interaction.

37. A probe as recited in claim 32 wherein said conductive layer is also formed for use in inducing and detecting non-optical interaction of said tip and said object.

38. A scanning probe microscopy probe comprising:

a base;

a cantilever connected to said base;

a tip connected to said cantilever;

clamping means for selectively clamping said cantilever rigid with respect to said base.

39. A probe as recited in claim 38 wherein said clamping means includes a clamping structure connected to said base and selectively moveable to clamp said cantilever rigid with respect to said base.

40. A probe as recited in claim 39 wherein:

said cantilever has a free end adjacent to said tip;

said clamping structure comprises a clamping arm extending from said base and having a free end extending past and opposing said free end of said cantilever, said free end of said clamping arm being moveable against said free end of said cantilever to selectively clamp said cantilever rigid with respect to said base.

41. A scanning probe as recited in claim 39 wherein said clamping structure surrounds said cantilever and includes clamping arms, said clamping arms being moveable against said cantilever to selectively clamp said cantilever rigid with respect to said base.

42. A probe as recited in claim 38 wherein:

said cantilever has a lower surface to which said tip is connected and an upper surface;

said clamping means includes:
- a member connected to said base having a lower surface disposed over said upper surface of said cantilever;
- an insulating layer on one of said upper surface of said cantilever and said lower surface of said member;
- wherein a voltage may be applied between said member and said cantilever to selectively electrostatically clamp said cantilever rigid with respect to said base.

43. A probe as recited in claim 38 wherein:

said cantilever has a lower surface to which said tip is connected and an upper surface;

said clamping means includes:
- a member coupled to said base and having a lower surface disposed over said upper surface of said cantilever;
- a first coil on said upper surface of said cantilever;
- a second coil on said lower surface of said member;
- wherein currents may be produced in said coils to selectively magnetically hold said cantilever rigid with respect to said base.

44. A probe as recited in claim 38 wherein:

said cantilever has a lower surface to which said tip is connected and an upper surface;

said clamping means includes:
- a member coupled to said base and having a lower surface disposed over said upper surface of said cantilever;
- a permanent magnet and a coil on different ones of said upper surface of said cantilever and said lower surface of said member; and
- wherein a current may be produced in said coil to selectively magnetically hold said cantilever rigid with respect to said base.

45. A scanning probe microscope assembly for examining an object, comprising:

a probe comprising a tip, said tip having a sharp end;

a light source optically coupled to said tip for providing light to said tip so that said provided light propagates in said tip;

rotationally polarizing means optically coupled between said light source and said tip for rotationally polarizing said provided light;

said tip being formed so as to emit said propagating light at said sharp end so that said emitted light optically interacts with said object a photodetector for detecting light that results from said emitted light optically interacting with said object; and deep surface feature analysis means coupled to said photodetector for identifying deep surface features from said detected light.

46. A scanning probe microscope assembly as recited in claim 45 wherein:

said tip has a base; and said scanning probe microscope assembly further comprises a lens optically coupled between said rotationally polarizing means and said tip for focusing said provided light in said base of said tip, said lens also being optically coupled between said tip and said photodetector for focusing said captured light for detection by said photodetector.

47. A scanning probe microscope assembly as recited in claim 46 wherein said lens comprises a fresnel lens formed in said probe.

48. A scanning probe microscope assembly as recited in claim 47 wherein said fresnel lens is disposed over said tip.

49. A scanning probe microscope assembly as recited in claim 45 wherein said scanning probe microscope assembly has a near-field optical microscopy mode and a near-field spectrophotometry mode and further comprises:

control means for controlling said rotationally polarizing means to rotationally polarize said provided light during said near-field optical microscopy mode and not during said near-field spectrophotometry mode; and a spectrophotometer including said light source and said photodetector for making spectrophotometric measurements of said detected light during said near-field spectrophotometry mode.

50. A scanning probe microscope assembly as recited in claim 45 wherein said lens comprises a refractive lens.

51. A scanning probe microscope assembly as recited in claim 50 wherein said refractive lens is disposed over said tip.

52. A scanning probe microscope assembly as recited in claim 45 wherein said rotationally polarizing means comprises a mechanically rotatable plane polarizer.

53. A scanning probe microscope assembly as recited in claim 45 wherein said rotationally polarizing means comprises a plane polarizer and means to rotate said object or said probe.

54. A scanning probe microscope assembly as recited in claim 45 wherein said rotationally polarizing means comprises an electro-optic mode shifter.

55. A scanning probe microscope assembly as recited in claim 45 further comprising non-optical interaction means for inducing and detecting non-optical interactions of said tip and said object.

56. A scanning probe microscope assembly as recited in claim 55 wherein:

said probe includes a cantilever connected to said tip; and said non-optical interaction means includes atomic force means for inducing atomic force interaction between said tip and said object means and for detecting deflection of said cantilever due to said atomic force interaction.

57. A scanning probe microscope assembly as recited in claim 55 wherein:

said tip includes:
- a core material that is transparent to said provided light so that said provided light propagates in said tip; and
- a conductive layer over said core material that is transparent to said propagating light at or not over said core material at said sharp end to form an aperture for emitting said propagating light;
- said non-optical interaction means includes tunneling current means for inducing and detecting a tunneling current between said tip and said object using said conductive layer.

58. A scanning probe microscopy probe comprising a tip having:

a sharp end;

an aperture at said sharp end of said tip for capturing light; and a photodiode formed in said tip for detecting the captured light.

59. A probe as recited in claim 58 wherein said photodiode comprises:

a first doped silicon region in said tip;

a second doped silicon region in said tip oppositely doped to and in contact with said first doped silicon region;

a first conductive coating in contact with said first doped silicon region; and a second conductive coating in contact with said second doped silicon region.

60. A probe as recited in claim 59 wherein:

said first doped silicon region is at said sharp end of said tip and said second doped silicon region is above said first doped silicon region;

said first conductive coating is transparent at or not over said sharp end of said tip to form said aperture.

61. A probe as recited in claim 58 further comprising a cantilever to which said tip is connected.

* * * * *